US012612415B2

(12) United States Patent
Okamoto et al.

(10) Patent No.: US 12,612,415 B2
(45) Date of Patent: Apr. 28, 2026

(54) STEREOSELECTIVE PROCESS FOR PREPARING SUBSTITUTED POLYCYCLIC PYRIDONE

(71) Applicant: Shionogi & Co., Ltd., Osaka (JP)

(72) Inventors: Kazuya Okamoto, Toyonaka (JP); Tatsuhiko Ueno, Toyonaka (JP); Yoshio Hato, Toyonaka (JP); Toshikazu Hakogi, Amagasaki (JP); Shohei Majima, Amagasaki (JP)

(73) Assignee: SHIONOGI & CO., LTD., Osaka (JP)

( * ) Notice: Subject to any disclaimer, the term of this patent is extended or adjusted under 35 U.S.C. 154(b) by 1011 days.

(21) Appl. No.: 17/679,449

(22) Filed: Feb. 24, 2022

(65) Prior Publication Data

US 2023/0040262 A1 Feb. 9, 2023

Related U.S. Application Data

(62) Division of application No. 16/652,122, filed as application No. PCT/JP2018/037390 on Oct. 5, 2018, now Pat. No. 11,286,262.

(30) Foreign Application Priority Data

Oct. 6, 2017 (JP) ................................ 2017-195802

(51) Int. Cl.
*C07D 498/14* (2006.01)
*C07C 215/10* (2006.01)
(Continued)

(52) U.S. Cl.
CPC .......... *C07D 498/14* (2013.01); *C07C 215/10* (2013.01); *C07D 213/89* (2013.01); *C07D 309/40* (2013.01); *C07B 2200/13* (2013.01)

(58) Field of Classification Search
CPC .................................................. C07D 498/14
(Continued)

(56) References Cited

U.S. PATENT DOCUMENTS

| | | |
|---|---|---|
| 6,426,418 B1 | 7/2002 | Tam et al. |
| 10,392,406 B2 | 8/2019 | Kawai et al. |

(Continued)

FOREIGN PATENT DOCUMENTS

| | | |
|---|---|---|
| CN | 104995198 | 10/2015 |
| CN | 107709321 | 2/2018 |

(Continued)

OTHER PUBLICATIONS

Stephen F. Martin et al., "Applications of Vinylogous Mannich Reactions. Asymmetric Synthesis of the Heteroyohimboid Alkaloids (−)-Ajmalicine, (+)-19-epi-Ajmalicine, and (−)-Tetrahydroalstonine", J. Org. Chem., 1995, vol. 60, No. 10, pp. 3236-3242.

(Continued)

*Primary Examiner* — Taofiq A Solola
(74) *Attorney, Agent, or Firm* — Wenderoth, Lind & Ponack, L.L.P.

(57) ABSTRACT

The present invention provides industrially suitable processes for preparing intermediates in the production of substituted polycyclic pyridone derivatives having a cap-dependent endonuclease inhibitory activity. In the process as shown below, wherein each symbol is as defined in the specification, an optically active substituted tricyclic pyridone derivative of the formula (VII) is obtained in high yield and high enantioselectivity by subjecting a compound of the formula (III) or (VI) to intramolecular cyclization with controlling stereochemistry to obtain a compound of the formula (IV) having a removable functional group on an asymmetric carbon, and then removing the functional group thereof;

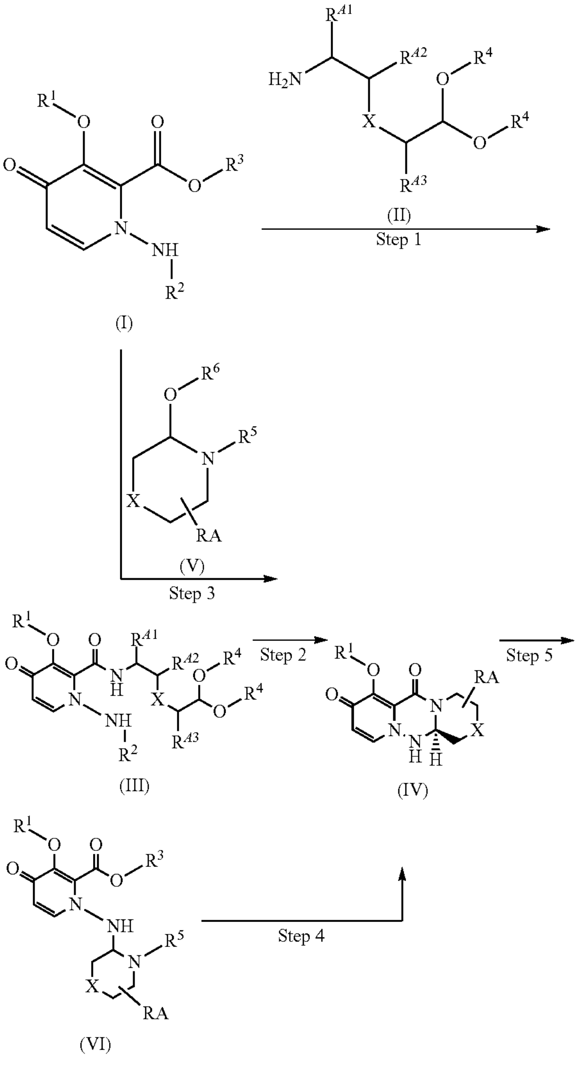

(I) (II) (V) (III) (IV) (VI)

(Continued)

-continued

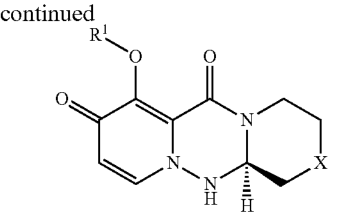

(VII)

2 Claims, 1 Drawing Sheet

(51) Int. Cl.
*C07D 213/89* (2006.01)
*C07D 309/40* (2006.01)

(58) Field of Classification Search
USPC .......................................................... 544/101
See application file for complete search history.

(56) References Cited

U.S. PATENT DOCUMENTS

| | | | |
|---|---|---|---|
| 2018/0118760 | A1 | 5/2018 | Kawai et al. |
| 2019/0169206 | A1 | 6/2019 | Kawai et al. |
| 2020/0261481 | A1 | 8/2020 | Shishido et al. |
| 2021/0230187 | A1 | 7/2021 | Shibahara et al. |

FOREIGN PATENT DOCUMENTS

| | | | |
|---|---|---|---|
| EP | 2 412 709 | 2/2012 | |
| EP | 2 444 400 | 4/2012 | |
| EP | 2 602 260 | 6/2013 | |
| EP | 2 620 436 | 7/2013 | |
| EP | 2 940 019 | 11/2015 | |
| EP | 3 290 424 | 3/2018 | |
| EP | 3 391 888 | 10/2018 | |
| EP | 3 473 629 | 4/2019 | |
| EP | 3 498 281 | 6/2019 | |
| WO | 2006/116764 | 11/2006 | |
| WO | 2007/002109 | 2/2007 | |
| WO | 2010/011812 | 1/2010 | |
| WO | 2010/011814 | 1/2010 | |
| WO | 2010/011815 | 1/2010 | |
| WO | 2010/011816 | 1/2010 | |
| WO | 2010/011818 | 1/2010 | |
| WO | 2010/011819 | 1/2010 | |
| WO | 2010/061282 | 6/2010 | |
| WO | 2010/067176 | 6/2010 | |
| WO | 2010/068253 | 6/2010 | |
| WO | 2010/068262 | 6/2010 | |
| WO | 2010/110409 | 9/2010 | |
| WO | 2 540 720 | 1/2013 | |
| WO | WO-2013164801 A1 * | 11/2013 | .............. A61P 43/00 |
| WO | 2014/099586 | 6/2014 | |
| WO | 2014/100323 | 6/2014 | |
| WO | WO-2014111871 A1 * | 7/2014 | .............. A61P 35/00 |
| WO | 2014/128545 | 8/2014 | |
| WO | 2015/009927 | 1/2015 | |
| WO | 2015/019310 | 2/2015 | |
| WO | 2015/039348 | 3/2015 | |
| WO | 2015/089847 | 6/2015 | |
| WO | 2015/095258 | 6/2015 | |
| WO | 2015/110897 | 7/2015 | |
| WO | 2015/111080 | 7/2015 | |
| WO | 2015/177537 | 11/2015 | |
| WO | 2015/199167 | 12/2015 | |
| WO | 2016/092527 | 6/2016 | |
| WO | 2016/094198 | 6/2016 | |
| WO | 2016/125192 | 8/2016 | |
| WO | 2016/175224 | 11/2016 | |
| WO | 2017/087256 | 5/2017 | |
| WO | 2017/104691 | 6/2017 | |
| WO | 2017/221869 | 12/2017 | |
| WO | 2018/030463 | 2/2018 | |
| WO | 2019/141179 | 7/2019 | |

OTHER PUBLICATIONS

Steven M. Allin et al., "An Asymmetric Synthesis of Both Enantiomers of the Indole Alkaloid Deplancheine", J. Org. Chem., vol. 70, No. 1, (2005), pp. 357-359.

Qin Yin et al., "Asymmetric Synthesis of Tetrahydro-β-carbolines via Chiral Phosphoric Acid Catalyzed Transfer Hydrogenation Reaction", Organic Letters, vol. 15, No. 11, pp. S1-S73 (2013).

Johns et al., "Carbamoyl Pyridone HIV-1 Integrase Inhibitors 3. A Diastereomeric Approach to Chiral Nonracemic Tricyclic Ring Systems and the Discovery of Dolutegravir (S/GSK1349572) and (S/GSK1265744)", Journal of Medicinal Chemistry, 2013, 56(14), 5901-5916.

Kawasuji et al., "Carbamoyl Pyridone HIV-1 Integrase Inhibitors. 2. Bi- and Tricyclic Derivatives Result in Superior Antiviral and Pharmacokinetic Profiles", Journal of Medicinal Chemistry, 2013, 56(3), 1124-1135.

Pace et al., "The monoethyl ester of meconic acid is an active site inhibitor of HCV NS5B RNA-dependent RNA polymerase", Bioorganic & Medicinal Chemistry Letters, 2004, 14(12), 3257-3261.

Battah et al., "Hydroxypyridinone and 5-Aminolaevulinic Acid Conjugates for Photodynamic Therapy", Journal of Medicinal Chemistry, 2017, 60(8), 3498-3510.

Xie et al., "Synthesis, physico-chemical properties, and antimicrobial evaluation of a new series of iron(III) hexadentate chelators", Medicinal Chemistry Research, 2013, 22(5), 2351-2359.

Agrawal et al., "Zinc-Binding Groups Modulate Selective Inhibition of MMPs", ChemMedChem, 2008, 3(5), 812-820.

Ehrlich et al., "Total Syntheses and Biological Evaluation of 3-O-Methylfunicone and Its Derivatives Prepared by TMPZnCl—LiCl-Mediated Halogenation and Carbonylative Stille Cross-Coupling", European Journal of Organic Chemistry, 2013, 77-83.

Looker et al., "Synthesis of Aldehyde and Carboxylic Acid Derivatives from 2-Hydroxymethyl-3-hydroxy-4H-pyran-4-one (α-Hydroxymaltol)", J. Heterocyclic Chem., 1986, 23(1), 225-227.

Sankareswaran et al., "Identification and Control of Critical Process Impurities: An Improved Process for the Preparation of Dolutegravir Sodium", Organic Process Research & Development, vol. 20, No. 8, pp. 1461-1468.

International Search Report issued Dec. 25, 2018 in International Application (PCT) No. PCT/JP2018/037390.

Partial Supplementary European Search Report dated Jun. 1, 2021 in European Patent Application No. 18865221.8.

Extended European Search Report dated Oct. 4, 2021 in European Patent Application No. 18865221.8.

Reich, M.F., et al., "Pyrido[3,4-e]-1,2,4-triazines and Related Heterocycles as Potential Antifungal Agents", J. Medicinal Chemistry, vol. 32, No. 11, Jan. 1, 1989, pp. 2474-2485.

Boyer, J., et al., "Difluoromethylbenzoxazole Pyrimidine Thioether Derivatives: A Novel Class of Potent Non-Nucleoside HIV-1 Reverse Transcriptase Inhibitors", J. Medicinal Chemistry, vol. 54, No. 23, Dec. 8, 2011, pp. 7974-7985.

* cited by examiner

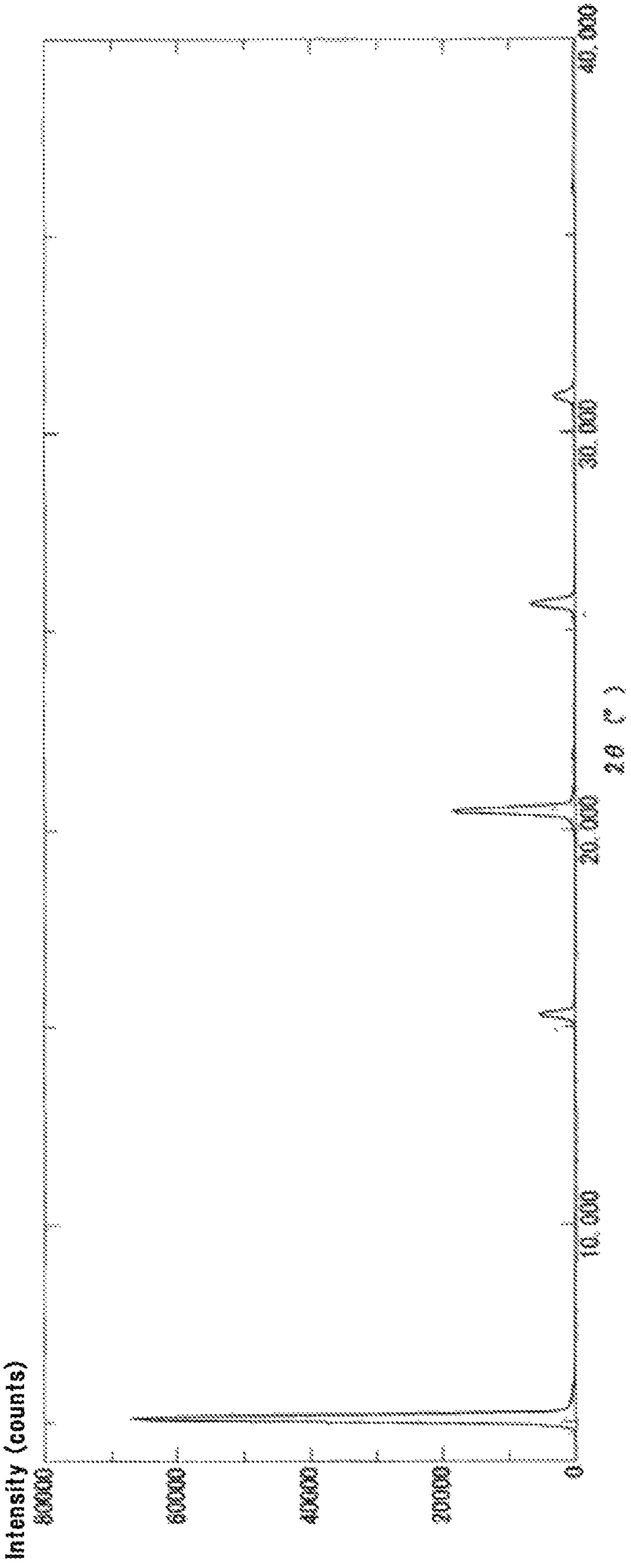
Intensity (counts)
80000
60000
40000
20000
0
10.000
20.000
30.000
40.000
2θ (°)

STEREOSELECTIVE PROCESS FOR PREPARING SUBSTITUTED POLYCYCLIC PYRIDONE

TECHNICAL FIELD

The present invention relates to a process for preparing substituted polycyclic pyridone derivatives. Specifically, the present invention relates to a stereoselective process for preparing substituted polycyclic pyridone derivatives and intermediates thereof.

BACKGROUND ART

It is known that a tricyclic pyridine derivatives such as 7-hydroxy-3,4,12,12a-tetrahydro-1H-[1,4]oxazino[3,4-c]pyrido[2,1-f][1,2,4]triazine-6,8-dione serves as a core skeleton of substituted polycyclic pyridone derivatives having cap-dependent endonuclease inhibitory activity and also as a common skeleton for other compounds useful as a medicament such as those compounds having HIV integrase inhibitory activity. Developments have been made to provide more industrially suitable methods for the synthesis of a common skeleton for such compounds useful as a medicament.

Also, developments have been made to provide efficient methods for manufacturing a pyrone compound as a raw material for the production of such common skeleton.

Patent Documents 1 to 14 disclose a stereoselective process for preparing Doltegravir using (R)-aminoalcohol shown below.

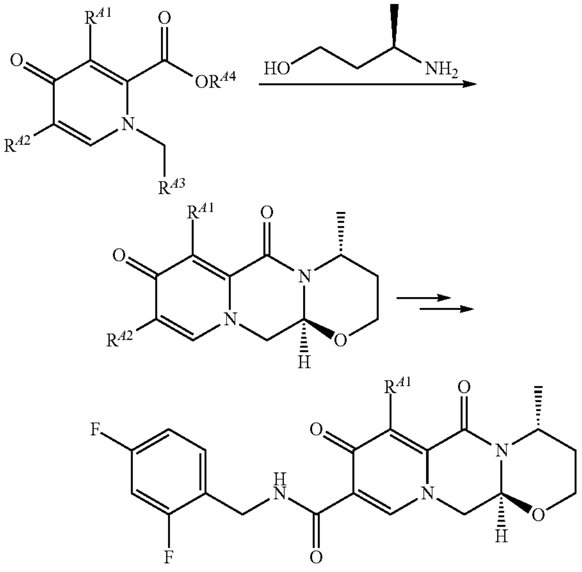

wherein $R^{A1}$ is hydroxyl, alkyloxy, halogen or the like; $R^{A2}$ is hydrogen, difluorobenzylcarbamoyl, alkyloxycarbonyl, carboxy or the like; $R^{A3}$ is aldehyde or aldehyde equivalent; $R^{A4}$ is alkyl or the like.

Patent Document 15 and Non-Patent Document 1 disclose a stereoselective process for preparing Doltegravir and its derivatives using optically active aminoalcohol or diamine shown below.

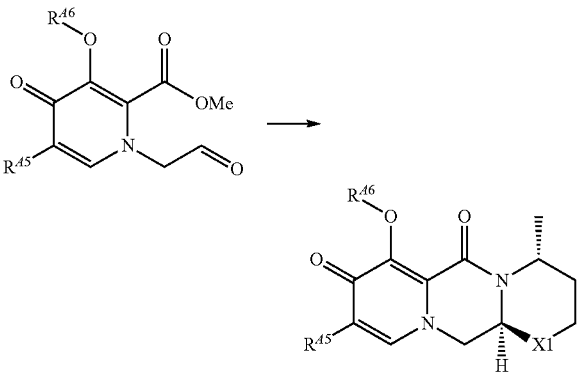

wherein $R^{A5}$ is difluorobenzylcarbamoyl; $R^{A6}$ is a protecting group for hydroxyl group; X1 is O or $NR^{A7}$; $R^{A7}$ is alkyl or the like; the other symbols are the same as defined above.

Patent Document 16 and Non-Patent Document 2 disclose a process for preparing racemic Doltegravir derivatives using aminoalcohol or diamine shown below.

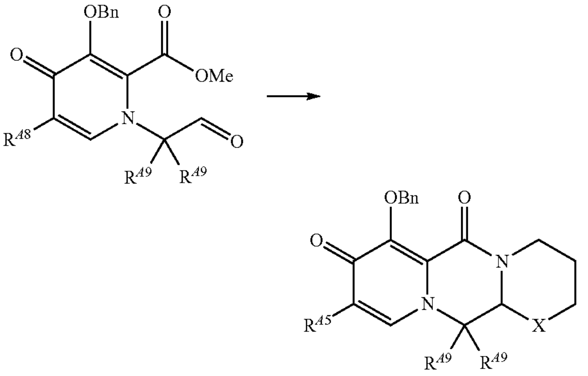

wherein $R^{A8}$ is hydrogen or difluorobenzylcarbamoyl; $R^{A9}$ is hydrogen or two $R^{A9}$ may be taken together with an adjacent carbon atom to form carbocycle or heterocycle; the other symbols are the same as defined above.

However, the above documents do not describe a process for preparing (R)-7-hydroxy-3,4,12,12a-tetrahydro-1-[1,4]oxazino[3,4-c]pyrido[2,1]-[1,2,4]triazine-6,8-dione.

Patent Document 17 discloses a process for preparing enantio mixture of 7-(benzyloxy)-3,4,12,12a-tetrahydro-1H-[1,4]oxazino[3,4-c]pyrido[2,1-f][1,2,4]triazine-6,8-dione shown below. Wavy line means enantio mixture (1:1).

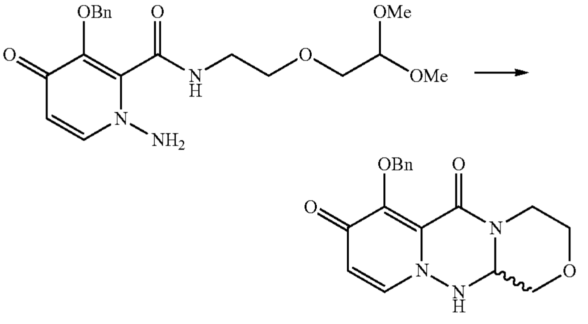

Patent Document 18 discloses a process for preparing the enantio mixture shown below.

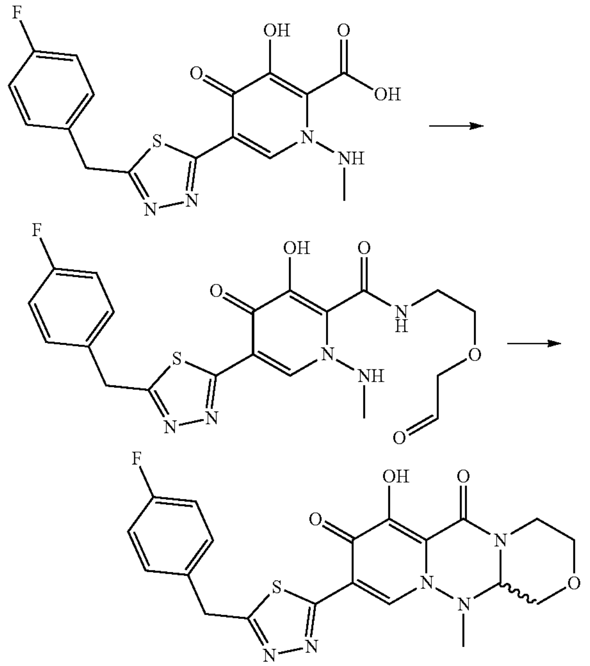

However, Patent Documents 17 and 18 do not describe a process for preparing optically active compound of 7-hydroxy-3,4,12,12a-tetrahydro-1-[1,4]oxazino[3,4-c]pyrido[2,1-f][1,2,4]triazine-6,8-dione.

Patent Documents 19 to 20 disclose a process that the enantio mixture of 7-(benzyloxy)-3,4,12,12a-tetrahydro-1-[1,4]oxazino[3,4-c]pyrido[2,1]-[1,2,4]triazine-6,8-dione, followed by optical resolution to give an optically active substance shown below. However, this process is not efficient because the compound having desired stereo configuration is obtained once the enantiomer mixture (1:1) is synthesized.

Also, Patent Documents 19 to 20 disclose a process for preparing 7-hydroxy-3,4,12,12a-tetrahydro-1-[1,4]oxazino[3,4-c]pyrido[2,1-f][1,2,4]triazine-6,8-dione which is substituted by methyl on the carbon adjacent to amide. After the introduction of Boc, the optically active compound is isolated and then deprotected to obtain the desired product.

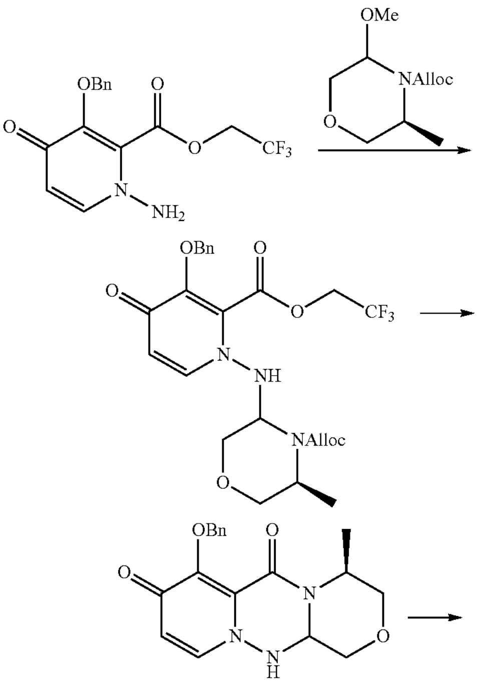

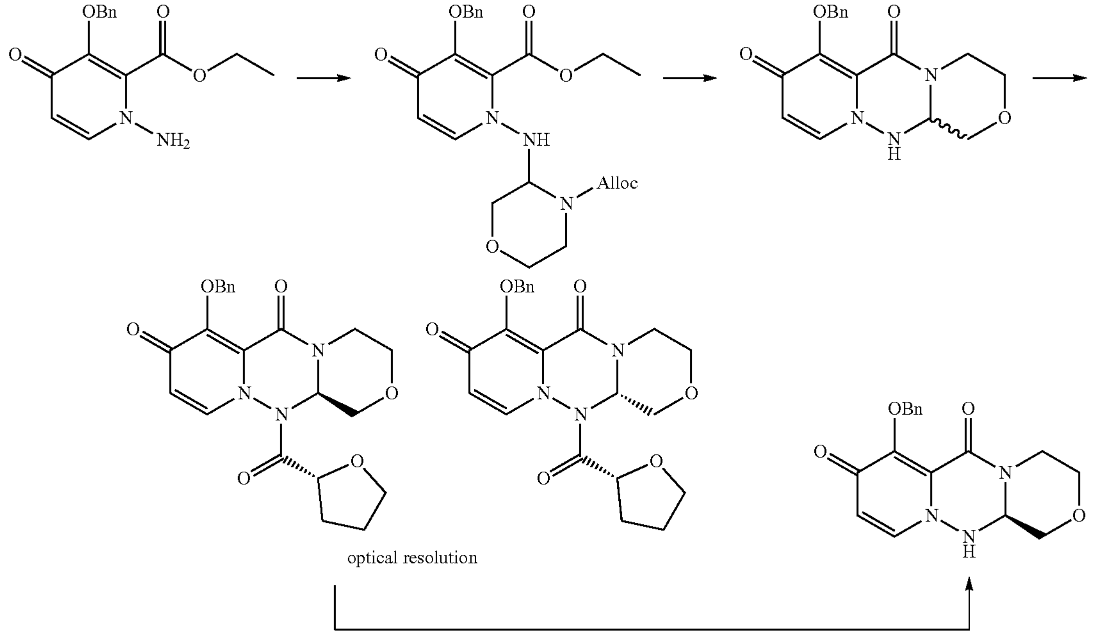

-continued

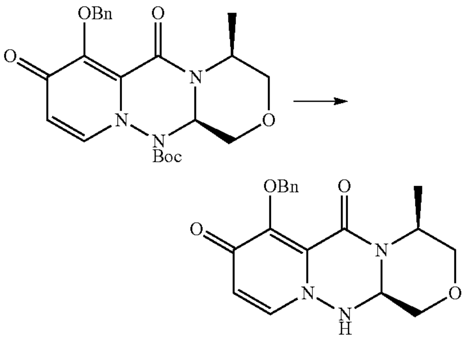

However, there is neither description nor suggestion of anything for a stereoselective synthesis of 7-hydroxy-3,4,12,12a-tetrahydro-1-[1,4]oxazino[3,4-c]pyrido[2,1-f][1,2,4]triazine-6,8-dione by introducing a substituent on the carbon adjacent to amide. In addition, there is neither description nor suggestion of any process in which a substituent which can be removed is introduced and then the substituent is removed to obtain optically active compounds of 7-hydroxy-3,4,12,12a-tetrahydro-1H-[1], oxazino[3,4-c]pyrido[2,1]-[1,2,4]triazine-6,8-dione.

Patent Document 21 also discloses similar process, although it is unpublished at the priority date of the present application.

Patent Documents 3, 4, 22, 23 and Non-Patent Documents 3 to 7 disclose a process, as follows, for preparing a pyrone compound by direct oxidation of maltol. However, selenium dioxide is a toxic reagent, and therefore, is not suitable for industrial production.

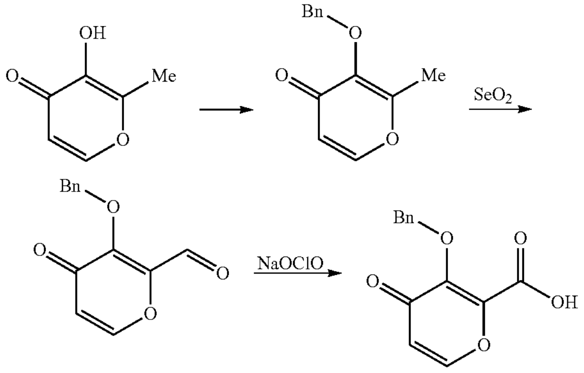

Patent Documents 1 to 4 and 24 to 29 disclose a process, as follows, wherein the oxidation of maltol is carried out via olefin. However, the process involves a reaction under low temperature at −70° C. in the second step, and therefore, requires special equipment for industrial production.

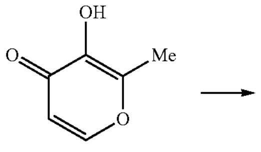

-continued

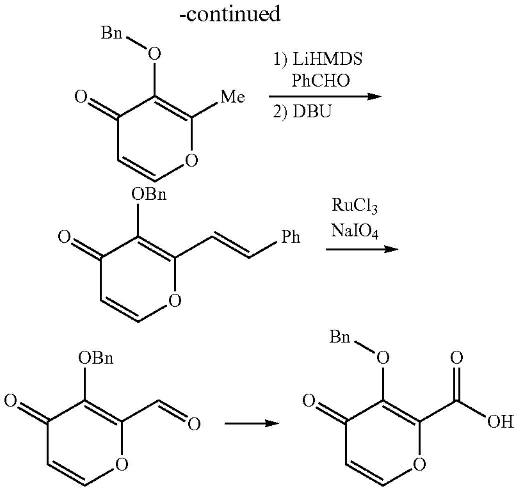

Patent Documents 6, 18 and 30 to 36 disclose a process comprising condensation reaction as follows. However, these documents disclose examples only for a pyrone compound having ester, amide or hetero ring at α-position of the carbonyl group but not disclose a pyrone compound having hydrogen at α-position of the carbonyl group.

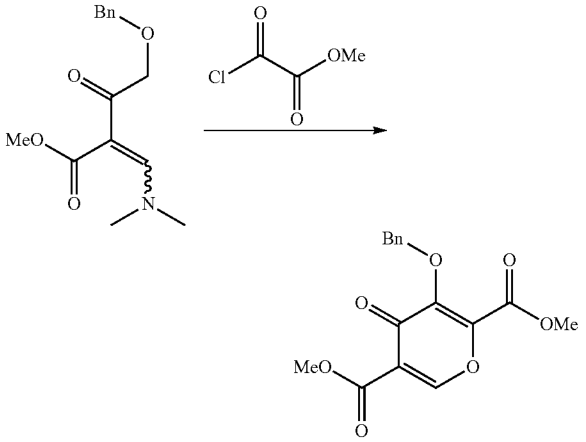

Patent Document 19 disclose a process for the production of an aminopyridone compound, comprising direct reaction with Boc-hydrazine, as shown below.

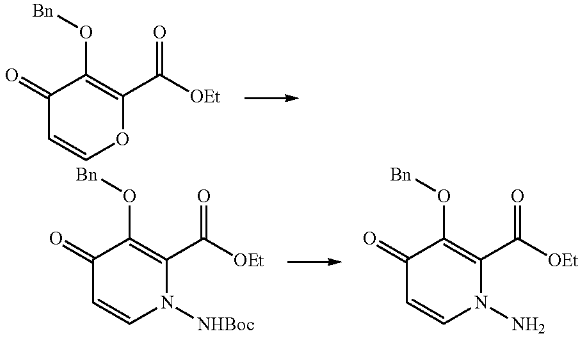

Patent Document 5 discloses a process for the production of an aminopyridone compound via a pyridone, as shown below. The process differs from the process herein disclosed in that the side chain of the pyridone contains amide in the step to obtain aminopyridone.

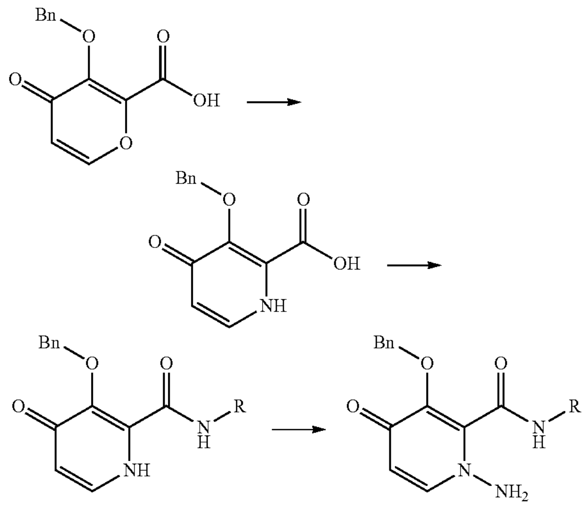

PRIOR ART DOCUMENTS

Patent Documents

Patent Document 1: WO2010/011812
Patent Document 2: WO2010/011819
Patent Document 3: WO2010/068253
Patent Document 4: WO2010/068262
Patent Document 5: WO2010/110409
Patent Document 6: WO2012/018065
Patent Document 7: WO2014/128545
Patent Document 8: WO 2015/009927
Patent Document 9: WO 2015/019310
Patent Document 10: WO 2015/110897
Patent Document 11: WO 2015/111080
Patent Document 12: WO 2015/177537
Patent Document 13: WO 2016/092527
Patent Document 14: WO 2016/125192
Patent Document 15: WO 2006/116764
Patent Document 16: WO 2016/094198
Patent Document 17: WO 2012/039414
Patent Document 18: WO 2014/099586
Patent Document 19: WO 2016/175224
Patent Document 20: WO 2017/104691
Patent Document 21: PCT/JP2017/28923
Patent Document 22: WO 2006/116764
Patent Document 23: WO 2007/002109
Patent Document 24: WO 2010/011814
Patent Document 25: WO 2010/011815
Patent Document 26: WO 2010/011816
Patent Document 27: WO 2010/011818
Patent Document 28: WO 2010/067176
Patent Document 29: WO 2015/039348
Patent Document 30: WO 2011/105590
Patent Document 31: WO 2010/110409
Patent Document 32: WO 2010/147068
Patent Document 33: WO 2014/104279
Patent Document 34: WO 2015/095258
Patent Document 35: WO 2015/089847
Patent Document 36: WO 2015/199167

Non-Patent Documents

Non-Patent Document 1: Journal of Medicinal Chemistry, 2013, 56(14), 5901-5916
Non-Patent Document 2: Journal of Medicinal Chemistry, 2013, 56(3), 1124-1135
Non-Patent Document 3: Bioorganic & Medicinal Chemistry Letters, 2004, 14(12), 3257-3261
Non-Patent Document 4: Journal of Medicinal Chemistry, 2017, 60(8), 3498-3510
Non-Patent Document 5: Medicinal Chemistry Research, 2013, 22(5), 2351-2359
Non-Patent Document 6: ChemMedChem, 2008, 3(5), 812-820
Non-Patent Document 7: Medicinal Chemistry Research, 2013, 22(5), 2351-2359; 2013

SUMMARY

The present invention provides an efficient method for preparing important intermediates for the production of substituted polycyclic pyridone derivatives, which are specifically a compound of the formula (VIII) or (IX) as disclosed herein or a salt thereof. Also, the present invention provides an efficient and more industrially suitable method for the production of a pyrone derivative and an aminopyridone derivative, as a raw material for the production of substituted polycyclic pyridone derivatives.

The present inventors have found efficient processes for the production of a compound of the formula (VII) which is an important intermediate for producing a compound of the formula (VIII) or (IX). That is, it has been found that an optically active tricyclic pyridone derivative of the formula (VII) can be obtained in a high yield with high enantioselectivity by intramolecular cyclization of a novel compound of the formula (III) or (VI) with controlled stereochemistry to obtain a novel compound of the formula (IV) having a removable functional group on an asymmetric carbon, and then removing the functional group.

In addition, it has been found a process for the production of novel compounds of the formula (III) and (VI).

Also, it has been found a novel process for the production of a compound of the formula (X3), (X8) or (V4).

That is, the present invention provides the following.

(1) A process for preparing a compound of the formula (VII), or a salt thereof:

(VII)

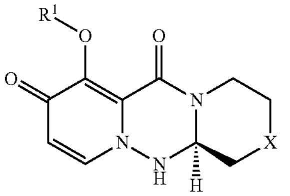

wherein $R^1$ is hydrogen or a protecting group for hydroxyl group; X is O or $CH_2$; characterized by removing —RA from a compound of the formula (IV):

(IV)

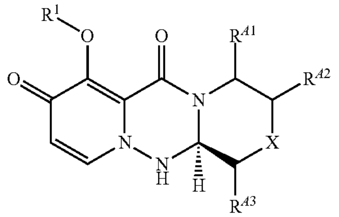

wherein $R^1$ is hydrogen or a protecting group for hydroxyl group; $R^{A1}$ is hydrogen or RA; $R^{A2}$ is hydrogen or RA; $R^{A3}$ is hydrogen or RA; X is O, $CH_2$ or CHRA; RA is a removable functional group; and the carbon atom to which RA is bound is optically active; provided that one of $R^{A1}$, $R^{A2}$ and $R^{A3}$ is RA, the other two are hydrogen, and X is O or $CH_2$, or $R^{A1}$, $R^{A2}$ and $R^{A3}$ are hydrogen and X is CHRA.

(2) A process for preparing a compound of the formula (IV), or a salt thereof:

(IV)

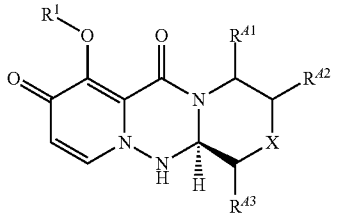

wherein each symbol is as defined below;
characterized by subjecting a compound of the formula (III) to intramolecular cyclization reaction:

(III)

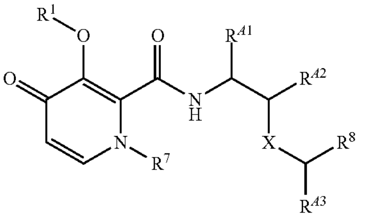

wherein $R^1$ is hydrogen or a protecting group for hydroxyl group; $R^{A1}$ is hydrogen or RA; $R^{A2}$ is hydrogen or RA; $R^{A3}$ is hydrogen or RA; X is O, $CH_2$ or CHRA; RA is a removable functional group and the carbon atom to which RA is bound is optically active; provided that one of $R^{A1}$, $R^{A2}$ and $R^{A3}$ is RA, the other two are hydrogen, and X is O or $CH_2$, or $R^{A1}$, $R^{A2}$ and $R^{A3}$ are hydrogen and X is CHRA; $R^7$ is $NH_2$ or $NHR^2$; $R^2$ is a protecting group for amino group; $R^8$ is —CHO or —$CH(OR^4)(OR^4)$; $R^4$ is each independently hydrogen or a protecting group deprotectable by an acid, or two $R^4$ may be taken together to form a ring.

(3) The process for preparing the compound of the formula (VII) or a salt thereof according to (1), which comprises the process according to (2).

(4) The process according to (2) or (3), wherein the intramolecular cyclization reaction is carried out in the presence of an acid.

(5) A process for preparing a compound of the formula (III) or a salt thereof:

(III)

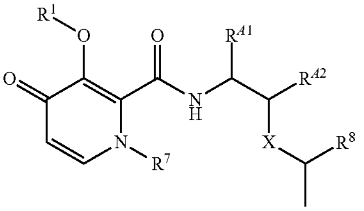

wherein each symbol is as defined below;
characterized by reacting a compound of the formula (Ia):

(Ia)

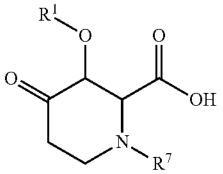

wherein $R^1$ is hydrogen or a protecting group for hydroxyl group; $R^7$ is $NH_2$ or $NHR^2$;
$R^2$ is a protecting group for amino group;
with a compound of the formula (II):

(II)

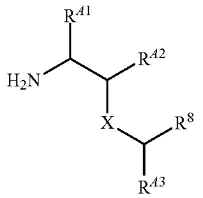

wherein $R^{A1}$ is hydrogen or RA; $R^{A2}$ is hydrogen or RA; $R^{A3}$ is hydrogen or RA; X is O, $CH_2$ or CHRA; RA is a removable functional group and the carbon atom to which RA is bound is optically active; provided that one of $R^{A1}$, $R^{A2}$ and $R^{A3}$ is RA, the other two are hydrogen, and X is O or $CH_2$, or $R^{A1}$, $R^{A2}$ and $R^{A3}$ are hydrogen and X is CHRA; $R^8$ is —CHO or —$CH(OR^4)(OR^4)$; $R^4$ is each independently hydrogen or a protecting group deprotectable by an acid, or two $R^4$ may be taken together to form a ring.

(6) A process for preparing a compound of the formula (IV) or a salt thereof:

(IV)

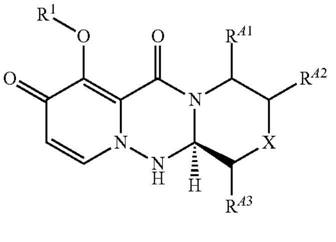

wherein each symbol is as defined below;

characterized by subjecting a compound of the formula (VI) to intramolecular cyclization reaction:

(VI)

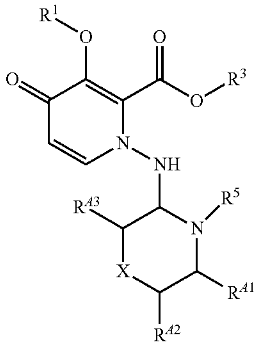

wherein $R^1$ is hydrogen or a protecting group for hydroxyl group; $R^{A1}$ is hydrogen or RA; $R^{A2}$ is hydrogen or RA; $R^{A3}$ is hydrogen or RA; X is O, $CH_2$ or CHRA; RA is a removable functional group and the carbon atom to which RA is bound is optically active; provided that one of $R^{A1}$, $R^{A2}$ and $R^{A3}$ is RA, the other two are hydrogen, and X is O or $CH_2$, or $R^{A1}$, $R^{A2}$ and $R^{A3}$ are hydrogen and X is CHRA; $R^3$ is a protecting group for carboxyl group; $R^5$ is hydrogen or a protecting group for amino group.

(7) The process for preparing the compound of the formula (VII) or a salt thereof according to (1), which comprises the process according to (6).

(8) The process according to (6) or (7), wherein the intramolecular cyclization reaction is carried out in the presence of a base.

(9) A process for preparing a compound of the formula (VI) or a salt thereof:

(VI)

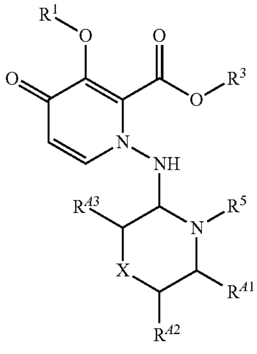

wherein each symbol is as defined below;

characterized by reacting a compound of the formula (Ib):

(Ib)

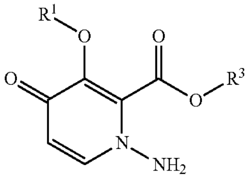

wherein $R^1$ is hydrogen or a protecting group for hydroxyl group; $R^3$ is a protecting group for carboxyl group; with a compound of the formula (V):

(V)

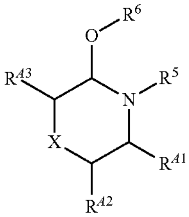

wherein $R^5$ is a protecting group for amino group; $R^6$ is substituted or unsubstituted alkyl, or substituted or unsubstituted aromatic carbocyclyl; $R^{A1}$ is hydrogen or RA; $R^{A2}$ is hydrogen or RA; $R^{A3}$ is hydrogen or RA; X is O, $CH_2$ or CHRA; RA is a removable functional group and the carbon atom to which RA is bound is optically active; provided that one of $R^{A1}$, $R^{A2}$ and $R^{A3}$ is RA, the other two are hydrogen, and X is O or $CH_2$, or $R^{A1}$, $R^{A2}$ and $R^{A3}$ are hydrogen and X is CHRA.

(10) The process according to any one of (1) to (9), wherein $R^{A1}$ is RA, and RA is optionally protected carboxy, or silyl-type functional group.

(11) A process for preparing a compound of the formula (X3) or a salt thereof:

(X3)

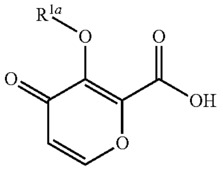

wherein each symbol is as defined below, comprising (Step 1) reacting a compound of the formula (X):

(X)

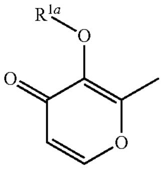

wherein $R^{1a}$ is a protecting group for hydroxyl group except optionally substituted aromatic carbocyclylalkyl and optionally substituted aromatic heterocyclylalkyl, with a halogenating agent to obtain a compound of the formula (X1):

(X1)

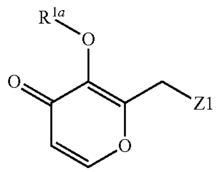

wherein $Z^1$ is halogen, and the other symbol is as defined above;

(Step 2) reacting the compound of the formula (X1) with hydroxide ion to obtain a compound of the formula (X2):

(X2)

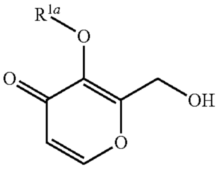

wherein each symbol is as defined above; and (Step 3) reacting the compound of the formula (X2) with an oxidizing agent to obtain the compound of the formula (X3).

(12) The process according to (11) wherein the halogenating agent is NBS, NCS, NIS, $Br_2$, $Cl_2$, $I_2$ or DBDMH, and the solvent in Step 1 is methyl acetate, ethyl acetate, propyl acetate or acetonitrile.

(13) The process according to (11) or (12) wherein the oxidizing agent is sodium hypochlorite.

(14) A process for preparing a compound of the formula (X8) or a salt thereof:

(X8)

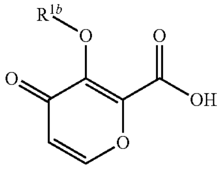

wherein each symbol is as defined below, comprising (Step 1) reacting a compound of the formula (X4):

(X4)

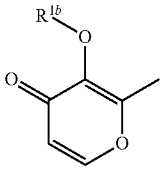

wherein $R^{1b}$ is a protecting group for hydroxyl group, with a compound of the formula:

(X5)

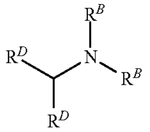

or (X5')

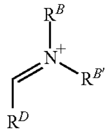

wherein each $R^B$ is independently alkyl optionally substituted by a group selected from Substituent Group E, or aromatic carbocyclyl optionally substituted by a group selected from Substituent Group E, or the two $R^B$ may be taken together with an adjacent nitrogen atom to form a heterocycle optionally substituted by a group selected from Substituent Group E; each $R^D$ is independently alkyloxy or dialkylamino;

Substituent Group E comprises halogen, hydroxy, sulfanyl, amino, alkyl, haloalkyl, alkyloxy, alkylsulfanyl, alkylsilyl, aromatic carbocyclylsilyl optionally substituted by a group selected from Substituent Group F, carbocyclyl optionally substituted by a group selected from Substituent Group F, heterocyclyl optionally substituted by a group selected from Substituent Group F, a carbocyclylalkyloxy optionally substituted by a group selected from Substituent Group F, heterocyclylalkyloxy optionally substituted by a group selected from Substituent Group F, carbocyclylalkylsulfanyl optionally substituted by a group selected from Substituent Group F, heterocyclylalkylsulfanyl optionally substituted by a group selected from Substituent Group F, carbocyclylalkylamino optionally substituted by a group selected from Substituent Group F, heterocyclylalkylamino optionally substituted by a group selected from Substituent Group F, carbocyclyloxy optionally substituted by a group selected from Substituent Group F, heterocyclyloxy optionally substituted by a group selected from Substituent Group F, haloalkyloxy, alkyloxyalkyl, alkyloxyalkyloxy, alkyloxycarbonylamino, alkylamino, alkylcarbonylamino, alkylsulfonyl and alkylsulfonylamino;

Substituent Group F comprises halogen, hydroxy, amino, oxo, nitro, alkyl, haloalkyl, alkyloxy and a protecting group for amino group;

to obtain a compound of the formula (X6):

(X6)

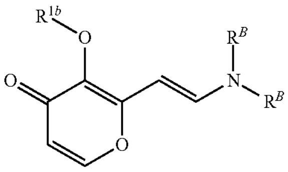

wherein each symbol is as defined above;

(Step 2) reacting the compound of the formula (X6) with an oxidizing agent to obtain a compound of the formula (X7):

(X7)

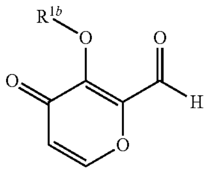

wherein each symbol is as defined above; and (Step 3) reacting the compound of the formula (X7) with an oxidizing agent to obtain the compound of the formula (X8).

(15) The process according to (14) wherein the Step 1 is carried out in the presence of a base.

(16) The process according to (14) or (15) wherein the oxidizing agent is sodium periodate.

(17) A process for preparing a compound of the formula (V4) or a salt thereof:

(V4)

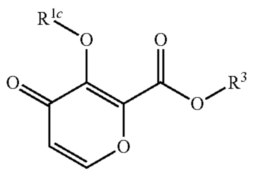

wherein each symbol is as defined below, comprising (Step 1) reacting a compound of the formula (X9):

(X9)

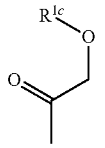

wherein $R^1$, is hydrogen or a protecting group for hydroxyl group, with a compound of the formula:

(V1)

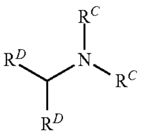

or (V1')

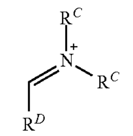

wherein each $R^C$ is independently alkyl optionally substituted by a group selected from Substituent Group E, or aromatic carbocyclyl optionally substituted by a group selected from Substituent Group E, or the two $R^C$ may be taken together with an adjacent nitrogen atom to form a heterocycle optionally substituted by a group selected from Substituent Group E; each $R^D$ is independently alkyloxy or dialkylamino; Substituent Group E is as defined above in (14)

to obtain a compound of the formula (V2):

(V2)

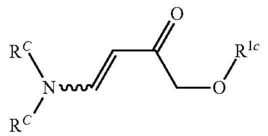

wherein the wavy line represents E- or Z-form or a mixture thereof, and the other symbols are as defined above;

(Step 2) subjecting the compound of the formula (V2) to intramolecular cyclization reaction by reacting with a compound of the formula (V3):

(V3)

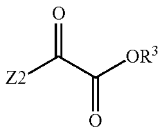

wherein $R^3$ is alkyl optionally substituted by a group selected from Substituent Group E, aromatic carbocyclylalkyl optionally substituted by a group selected from Substituent Group B; and Z2 is hydrogen, halogen or alkyloxy optionally substituted by a group selected from Substituent Group E, to obtain a compound of the formula (V4).

(18) The process according to (17) wherein the Step 1 is carried out using DMSO as a solvent in the presence of an additive agent.

(19) The process according to (17) or (18) wherein the intramolecular cyclization reaction is carried out in the presence of an acid under anhydrous condition.

(20) A process for preparing a compound of the formula (V7) or a salt thereof:

(V7)

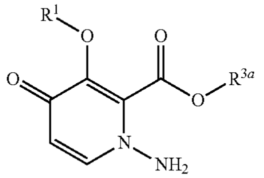

wherein each symbol is as defined below, comprising reacting a compound of the formula (V6):

(V6)

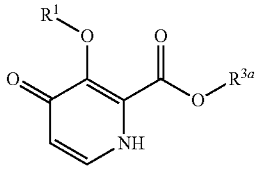

wherein $R^1$ is hydrogen or a protecting group for hydroxyl group; and $R^{3a}$ is hydrogen or a protecting group for carboxyl group with a hydroxylamine derivative.

(21) A process for preparing a compound of the formula (V7) or a salt thereof:

(V7)

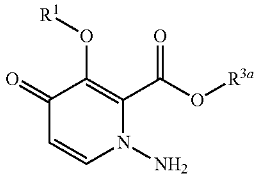

wherein each symbol is as defined below, comprising (Step 1) reacting a compound of the formula (V5):

(V5)

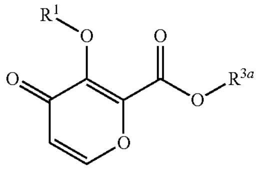

wherein $R^1$ is hydrogen or a protecting group for hydroxyl group, and $R^{3a}$ is hydrogen or a protecting group for carboxyl group with ammonia to obtain a compound of the formula (V6);

(V6)

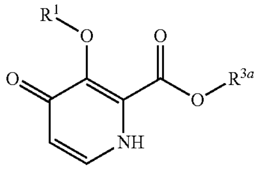

wherein each symbol is as defined above; and (Step 2) reacting the compound of the formula (V6) with a hydroxylamine derivative to obtain the compound of the formula (V7).

(22) The process according to (20) or (21), wherein the reaction with a hydroxylamine derivative is carried out in the presence of a base.

(23) The process according to (20) or (21), wherein the hydroxylamine derivative is hydroxylamine-O-sulfonic acid or O-(2,4-dinitrophenyl)hydroxylamine.

(24) A process for preparing a compound of the formula (VIIIa) or the formula (IXa), or a salt thereof:

(VIIIa)

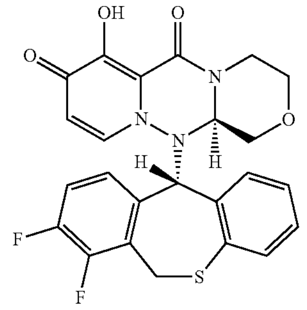

or (IXa)

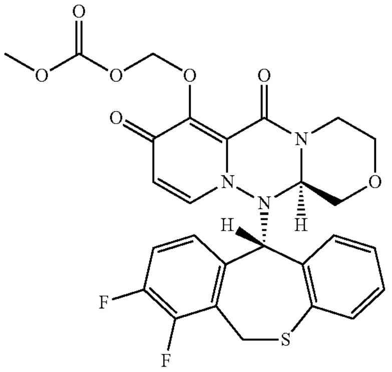

which comprises the process according to any one of (1) to (23).

(25) A compound of the formula (III) or a salt thereof:

(III)

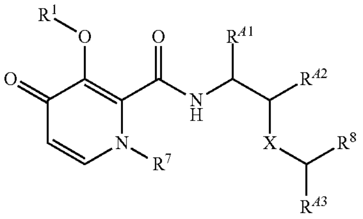

wherein each symbol is as defined in (2).

(26) A compound of the formula (VI) or a salt thereof:

(VI)

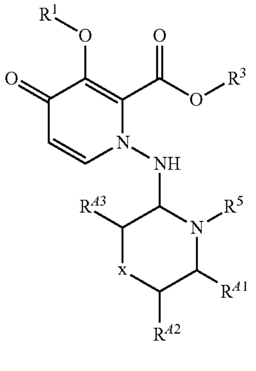

wherein each symbol is as defined in (6).

(27) A compound of the formula (IV) or a salt thereof:

(IV)

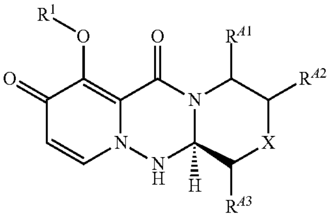

wherein each symbol is as defined in (1).

(28) A crystal of phosphate, methanesulfonate or p-chlorobenzoate salt of the compound of the formula:

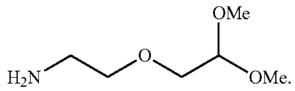

(29) The crystal according to (28) which is a crystal of the phosphate salt.

(30) The crystal according to (29) characterized by an X-ray powder diffraction spectrum comprising peaks at diffraction angle (2θ) of 5.1°±0.2°, 15.3°±0.2°, 20.5°±0.2°, 25.7°±0.2° and 30.9°±0.2°.

(31) The crystal according to (29) characterized by an X-ray powder diffraction spectrum comprising peaks at diffraction angle (2θ) of 5.1°±0.2°, 10.2°±0.2°, 15.3°±0.2°, 20.5°±0.2°, 21.8°±0.2°, 25.7°±0.2°, 30.9°±0.2° and 36.3°±0.2°.

(32) The crystal according to (29) characterized by an x-ray powder diffraction spectrum substantially in accordance with that shown in FIG. 1.

The process of the present invention enables efficient production of a polycyclic pyridone derivative of the formula (VIII) or (IX) with high optical purity.

One of the features of the present invention is that a carbon atom is substituted with RA, and then said RA is removed.

A compound of the formula (IV) can be produced selectively by intramolecular cyclization using an optically active compound of the formula (III) or (VI). The selectivity is about 2 to 30 times. In particular, when $R^{A1}$ is RA, which is a protected carboxy, the compound of the formula (VI) can be prepared with a selectivity of about 10 to 20 times.

BRIEF DESCRIPTION OF DRAWINGS

FIG. 1 is an X-ray powder diffraction spectrum of the crystal of phosphate salt of Compound 26.

MODE FOR CARRYING OUT THE INVENTION

The meaning of each term used in the present description is explained below. Unless otherwise specified, each term has the same meaning when used alone or in combination with another term.

The term "consisting of" or "consists of" means that the named element(s) is included exclusively.

The term "including", "include", "comprising" or "comprises" means to include, but not limited to, the named element(s), i.e., other element(s) is not excluded.

The term "optionally substituted by a group selected from Substituent Group A" means that any position may be substituted by one, two or more same or different groups selected from Substituent Group A.

The same applies to the terms "optionally substituted by a group selected from Substituent Group B", "optionally substituted by a group selected from Substituent Group C", "optionally substituted by a group selected from Substituent Group D", "optionally substituted by a group selected from Substituent Group E" and "optionally substituted by a group selected from Substituent Group F".

Substituent Group A: halogen, amino, alkylamino, alkylsulfonyl, aromatic carbocyclylsulfonyl, alkylsulfinyl, aromatic carbocyclylsulfinyl, nitro, alkyloxy, alkyloxycarbonyl, alkylcarbamoyl, and aromatic carbocyclyl.

Substituent Group B: halogen, amino, alkylamino, alkylsulfonyl, aromatic carbocyclylsulfonyl, alkylsulfinyl, aromatic carbocyclylsulfinyl, nitro, alkyl, haloalkyl, alkyloxy, alkyloxycarbonyl, alkylcarbamoyl, and aromatic carbocyclyl.

Substituent Group C: halogen, amino, alkylamino, alkyloxy, aromatic carbocyclyl.

Substituent Group D: halogen, amino, alkylamino, alkyl, alkyloxy, and aromatic carbocyclylic group.

Substituent Group E: halogen, hydroxy, sulfanyl, amino, alkyl, haloalkyl, alkyloxy, alkylsulfanyl, alkylsilyl, aromatic carbocyclylsilyl optionally substituted by a group selected from Substituent Group F, carbocyclyl optionally substituted by a group selected from Substituent Group F, heterocyclyl optionally substituted by a group selected from Substituent Group F, a carbocyclylalkyloxy optionally substituted by a group selected from Substituent Group F, heterocyclylalkyloxy optionally substituted by a group selected from Substituent Group F, carbocyclylalkylsulfanyl optionally substituted by a group selected from Substituent Group F, heterocyclylalkylsulfanyl optionally substituted by a group selected from Substituent Group F, carbocyclylalkylamino optionally substituted by a group selected from Substituent Group F, heterocyclylalkylamino optionally substituted by a group selected from Substituent Group F, carbocyclyloxy optionally substituted by a group selected from Substituent Group F, heterocyclyloxy optionally substituted by a group selected from Substituent Group F, haloalkyloxy, alkyloxyalkyl, alkyloxyalkyloxy, alkyloxycarbonylamino, alkylamino, alkylcarbonylamino, alkylsulfonyl, and alkylsulfonylamino.

Substituent Group F: halogen, hydroxy, amino, oxo, nitro, alkyl, haloalkyl, alkyloxy, and a protecting group for amino group.

The term "halogen" includes fluorine, chlorine, bromine or iodine. Fluorine and chlorine are preferable, and fluorine is especially preferable.

The term "alkyl" means a C1 to C6 straight or branched alkyl and includes C1 to C4 alkyl, C1 to C3 alkyl and the like. Examples include methyl, ethyl, n-propyl, isopropyl, n-butyl, isobutyl, sec-butyl, tert-butyl, n-pentyl, isopentyl, neopentyl, hexyl, isohexyl and the like.

The term "substituted or unsubstituted alkyl" in $R^6$ is not limited so long as it allows Step 3 of Scheme 5 in the general procedure described below to proceed efficiently. Examples include, but not limited to, alkyl optionally substituted by a group selected from Substituent Group A.

The term "haloalkyl" means the above "alkyl" substituted with one or more "halogen" described above. Examples include trifluoromethyl, trifluoroethyl and the like.

The term "alkylcarbamoyl" means a carbamoyl group substituted with one or two same or different "alkyl" described above on the nitrogen atom. Examples include methylcarbamoyl, ethylcarbamoyl, dimethylcarbamoyl, diethylcarbamoyl and the like.

The term "alkylamino" means an amino group substituted with one or two same or different "alkyl" described above on the nitrogen atom. Examples include methylamino, ethylamino, dimethylamino, diethylamino and the like.

The term "alkylsilyl" means a group wherein one, two or three same or different "alkyl" described above is substituted on the silyl. Examples include methylsilyl, ethylsilyl, dimethylsilyl, diethylsilyl, methylethylsilyl, trimethylsilyl and the like.

The term "carbocyclyl" means "aromatic carbocyclyl" or "non-aromatic carbocyclyl".

The term "carbocycle" means a ring derived from "carbocyclyl" described above.

The term "heterocyclyl" means "aromatic heterocyclyl" or "non-aromatic heterocyclyl".

The term "heterocycle" means a ring derived from "heterocyclyl" described above.

The term "aromatic carbocyclyl" means a monocyclic or polycyclic aromatic hydrocarbon group. Examples include phenyl, naphthyl, anthryl, phenanthryl and the like.

A preferred embodiment of "aromatic carbocyclyl" is phenyl or naphtyl.

The term "substituted or unsubstituted aromatic carbocyclyl" in $R^6$ is not limited so long as it allows Step 3 of Scheme 5 in the general procedure described below to proceed. Examples include, but not limited to, aromatic carbocyclyl optionally substituted by a group selected from Substituent Group B.

The term "aromatic carbocycle" means a ring derived from "aromatic carbocyclyl" described above.

The term "non-aromatic carbocyclyl" means a monocyclic or polycyclic saturated hydrocarbon group or unsaturated non-aromatic hydrocarbon group. The "non-aromatic carbocyclyl" which is polycyclic includes a fused ring group wherein a non-aromatic carbocyclyl, which is monocyclic or polycyclic, is fused with a ring of the above "aromatic carbocyclyl".

In addition, examples of the "non-aromatic carbocyclyl" also include a group having a bridge or a group to form a spiro ring as follows:

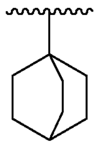
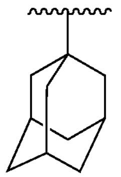
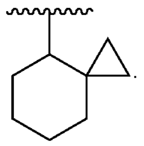

The non-aromatic carbocyclyl which is monocyclic is preferably C3 to C16, more preferably C3 to C12 and further preferably C4 to C8 carbocyclyl. Examples include cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, cyclohexadienyl and the like.

Examples of non-aromatic carbocyclyl, which is polycyclic, include indanyl, indenyl, acenaphthyl, tetrahydronaphthyl, fluorenyl and the like.

The term "non-aromatic carbocycle" means a ring derived from "non-aromatic carbocyclyl" described above.

The term "aromatic heterocyclyl" means an aromatic cyclyl, which is monocyclic or polycyclic, containing one or more, same or different heteroatom(s) selected independently from O, S and N.

The "aromatic heterocyclyl", which is polycyclic, includes a fused ring group wherein an aromatic heterocyclyl, which is monocyclic or polycyclic, is fused with a ring of the above "aromatic carbocyclyl". The free valency from the "heterocyclyl" may be on either ring.

The aromatic heterocyclyl, which is monocyclic, is preferably 5- to 8-membered and more preferably 5- or 6-membered. Examples of 5-membered heterocyclyl include pyrrolyl, imidazolyl, pyrazolyl, triazolyl, tetrazolyl, furyl, thienyl, isoxazolyl, oxazolyl, oxadiazolyl, isothiazolyl, thiazolyl, thiadiazolyl and the like. Examples of 6-membered aromatic heterocyclyl include pyridyl, pyridazinyl, pyrimidinyl, pyrazinyl, triazinyl and the like.

The aromatic heterocyclyl, which is bicyclic, is preferably 8- to 10-membered and more preferably 9- or 10-membered. Examples include indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, thiazolopyridyl and the like.

The aromatic heterocyclyl, which is tricyclic or more, is preferably 13- to 15-membered. Examples include carbazolyl, acridinyl, xanthenyl, phenothiazinyl, phenoxathiinyl, phenoxazinyl, dibenzofuryl and the like.

The term "aromatic heterocycle" means a ring derived from "aromatic heterocyclyl" described above.

The term "non-aromatic heterocyclyl" means a non-aromatic cyclyl, which is monocyclic or polycyclic, containing one or more, same or different heteroatom(s) selected independently from O, S and N. The "non-aromatic heterocyclyl", which is polycyclic, include an above-mentioned non-aromatic heterocyclyl, which is monocyclic or polycyclic, fused with a ring of the above "aromatic carbocyclyl", "non-aromatic carbocyclyl" and/or "aromatic heterocyclyl" and also include an above-mentioned non-aromatic heterocyclyl, which is monocyclic or polycyclic, fused with a ring of the above "aromatic heterocyclyl", and the free valency may be on either ring.

In addition, Examples of the "non-aromatic heterocyclyl" includes a group having a bridge or a group to form a spiro ring as follows:

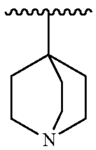
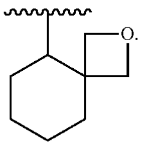

The non-aromatic heterocyclyl, which is monocyclic, is preferably 3- to 8-membered and more preferably 5- to 6-membered. Examples of non-aromatic heterocyclyl, which is 3-membered, include thiiranyl, oxiranyl and aziridinyl. Examples of non-aromatic heterocyclyl, which is 4-membered, include oxetanyl and azetidinyl. Examples of non-aromatic heterocyclyl, which is 5-membered, include oxathiolanyl, thiazolidinyl, pyrrolidinyl, pyrrolinyl, imidazolidinyl, imidazolinyl, pyrazolidinyl, pyrazolinyl, tetrahydrofuryl, dihydrothiazolyl, tetrahydroisothiazolyl, dioxolanyl, dioxolyl, thiolanyl and the like. Examples of non-aromatic heterocyclyl, which is 6-membered, include dioxanyl, thianyl, piperidyl, piperazinyl, morpholinyl, morpholino, thiomorpholinyl, thiomorpholino, dihydropyridyl, tetrahydropyridyl, tetrahydropyranyl, dihydrooxazinyl, tetrahydropyrandinyl, hexahydropyrimidinyl, dioxazinyl, thiynyl, thiazinyl and the like. Examples of non-aromatic heterocyclyl, which is 7-membered, include hexahydroazepinyl, tetrahydrodiazepinyl and oxepanyl.

The non-aromatic heterocyclyl, which is polycyclic, is preferably 8- to 20-membered and more preferably 8- to 10-membered. Examples include indolinyl, isoindolinyl, chromanyl, isochromanyl and the like.

The term “non-aromatic heterocycle” means a ring derived from “non-aromatic heterocyclyl” described above.

The term “protecting group for hydroxyl group” means a group replacing a hydrogen atom of a hydroxyl group, and a group which is deprotected by a general method, such as described in Protective Groups in Organic Synthesis, Theodora W Green (John Wiley & Sons), to generate hydroxyl group. Examples include aromatic carbocyclylalkyl optionally substituted by a group selected from Substituent Group B (e.g., benzyl, p-methoxyphenylbenzyl), alkylcarbonyl optionally substituted by a group selected from Substituent Group A (e.g., acetyl, pivaloyl, chloroacetyl), formyl, aromatic carbocyclylcarbonyl optionally substituted by a group selected from Substituent Group B (e.g., benzoyl), alkyloxycarbonyl optionally substituted by a group selected from Substituent Group A (e.g., methoxycarbonyl, isobutyloxycarbonyl, benzyloxycarbonyl, vinyloxycarbonyl), aromatic carbocyclyloxycarbonyl optionally substituted by a group selected from Substituent Group B (e.g., phenyloxycarbonyl), alkylsulfonyl optionally substituted by a group selected from Substituent Group A (e.g., mesyl), aromatic carbocyclylsulfonyl optionally substituted by a group selected from Substituent Group B (e.g., tosyl), trialkylsilyl (e.g., trimethylsilyl, triethylsilyl, t-butyldimethylsilyl), alkyloxyalkyl optionally substituted by a group selected from Substituent Group A (e.g., methoxymethyl, benzyloxymethyl, methoxyethoxymethyl), 2-(trimethylsilyl)ethoxymethyl, propenyl, phenacyl, tetrahydropyranyl, alkyl, and the like.

Examples of “a protecting group for hydroxyl group except optionally substituted aromatic carbocyclylalkyl and optionally substituted aromatic heterocyclylalkyl” in $R^{1a}$ include alkylcarbonyl optionally substituted by a group selected from Substituent Group A, formyl, aromatic carbocyclylcarbonyl optionally substituted by a group selected from Substituent Group B, alkyloxycarbonyl optionally substituted by a group selected from Substituent Group A, aromatic carbocyclyloxycarbonyl optionally substituted by a group selected from Substituent Group B, alkylsulfonyl optionally substituted by a group selected from Substituent Group A, aromatic carbocyclylsulfonyl optionally substituted by a group selected from Substituent Group B, trialkylsilyl, alkyloxyalkyl optionally substituted by a group selected from Substituent Group A, 2-(trimethylsilypethoxymethyl, propenyl, phenacyl, tetrahydropyranyl, alkyl and the like.

The term “protecting group for amino group” means a group replacing a hydrogen atom of an amino group, and a group which is deprotected by a general method, such as described in Protective Groups in Organic Synthesis, Theodora W Green (John Wiley & Sons), to generate amino group. Examples include trialkylsilyl (e.g., t-butyldimethylsilyl, 2,2,2-trichloroethoxycarbonyl), alkyloxycarbonyl optionally substituted by a group selected from Substituent Group A (e.g., t-butoxycarbonyl), aromatic carbocyclyloxycarbonyl optionally substituted by a group selected from Substituent Group B (e.g., benzyloxycarbonyl), aromatic carbocyclylalkyloxycarbonyl (e.g., 9-fluorenylmethyloxycarbonyl), aromatic carbocyclyloxycarbonyl, and the like.

As the “protecting group for amino group” in $R^2$, t-butyldimethylsilyl, t-butoxycarbonyl or benzyloxycarbonyl is preferable.

As the “protecting group for amino group” in $R^5$, Alloc or Fmoc is preferable.

The term “protecting group for carboxy group” means a group replacing a hydrogen atom of a carboxy group, and a group which is deprotected by a general method, such as described in Protective Groups in Organic Synthesis, Theodora W Green (John Wiley & Sons), to generate carboxy group. Examples include alkyl (e.g., methyl, ethyl, t-butyl), or aromatic carbocyclylalkyl optionally substituted by a group selected from Substituent Group B (e.g., benzyl).

The term “protecting group deprotectable by an acid” includes alkyl optionally substituted by a group selected from Substituent Group A and a ring wherein two $R^4$ may be taken together to form the ring. For example, when $R^4$ is alkyl, —CH($OR^4$)($OR^4$) is dialkyl acetal (preferred is dimethylacetal), which is well known as a protecting group for aldehyde. Also, when two $R^4$ may be taken together to form a ring, —CH($OR^4$)($OR^4$) is cyclic acetal, which is well known as a protecting group for aldehyde. These protecting groups can be deprotected by an acid and converted to —CHO.

The term “removable functional group” means a leaving group or a functional group which can be converted into a leaving group. Examples include optionally protected carboxy, optionally protected amino, optionally protected hydroxy, chlorine, bromine, iodine, or silyl-type functional group. Preferred is optionally protected carboxy, and more preferred is protected carboxy.

The term “optionally protected carboxy” means carboxy or a group which can be deprotected according to a general method, such as described in Protective Groups in Organic Synthesis, Theodora W Green (John Wiley & Sons), to generate carboxy group. Preferred is alkyloxycarbonyl optionally substituted by a group selected from Substituent Group A (e.g., methyloxycarbonyl, ethyloxycarbonyl).

The “optionally protected carboxy” may be deprotected to carboxy, which is then removed, or may be converted into “active ester”, which is then removed.

Examples of the “active ester” include those already reported, particularly, as an ester having high desorption ability, a group of the formula: —C(=O)—O—$R^9$ wherein $R^9$ is a group of the formula:

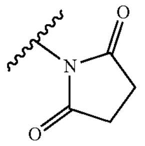
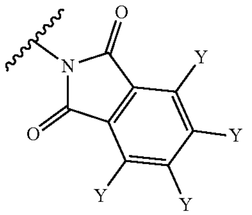
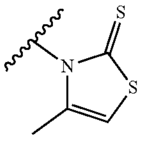

-continued

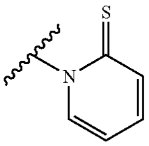 or 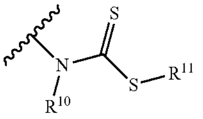

wherein Y is each independently hydrogen or halogen; $R^{10}$ is alkyl optionally substituted by a group selected from Substituent Group A or aromatic carbocyclyl optionally substituted by a group selected from Substituent Group B; $R^{11}$ is alkyl optionally substituted by a group selected from Substituent Group A or aromatic carbocyclyl optionally substituted by a group selected from Substituent Group B.

More preferred is a group of the following formula:

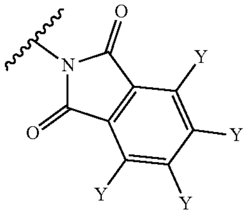 or 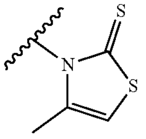

wherein each symbol is as defined above.

"Silyl-type functional group" is any substance may be used as long as it can be removed by fluoride ion reagent. Examples include a group of the formula: $—Si(R^{A4})_3$ wherein $R^{A4}$ is each independently alkyl optionally substituted by a group selected from Substituent Group A or aromatic carbocyclyl optionally substituted by a group selected from Substituent Group B.

Example of a compound the formula (IV):

(IV)

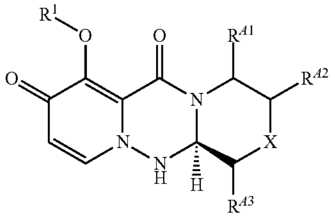

wherein "$R^{A1}$ is hydrogen or RA; $R^{A2}$ is hydrogen or RA; $R^{A3}$ is hydrogen or RA; X is O, $CH_2$ or CHRA; RA is a removable functional group; and the carbon atom to which RA is bound is optically active; provided that one of $R^{A1}$, $R^{A2}$ and $R^{A3}$ is RA, the other two are hydrogen and X is O or $CH_2$, or $R^{A1}$, $R^{A2}$ and $R^{A3}$ are hydrogen and X is CHRA" includes compounds of the formulae shown below.

(IVa)

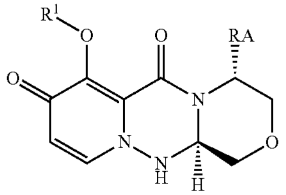

-continued (IVb)

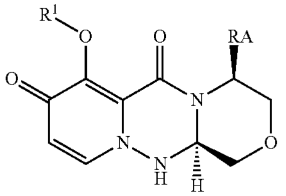

(IVc)

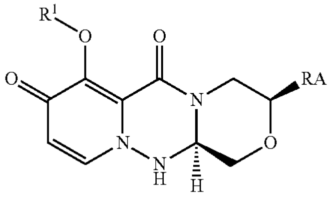

(IVd)

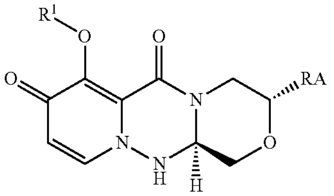

(IVe)

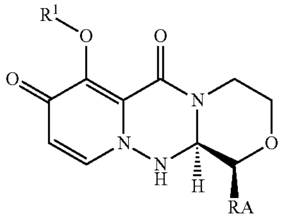

(IVf)

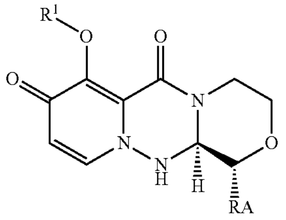

(IVg)

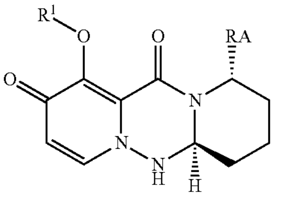

(IVh)

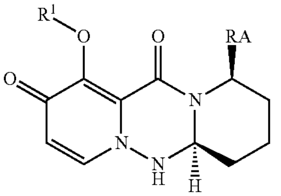

-continued (IVi)

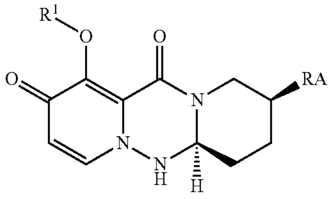

(IVj)

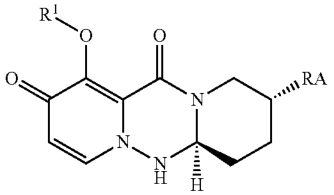

(IVk)

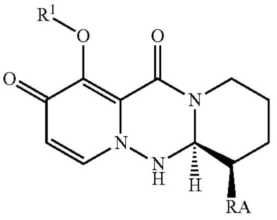

(IVl)

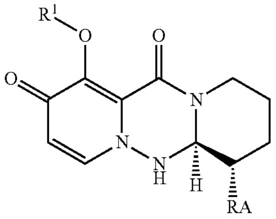

(IVm)

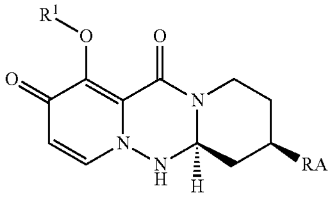

(IVn)

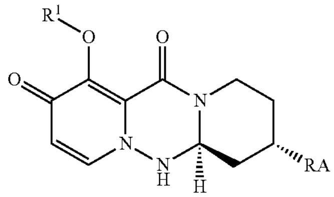

In particular, it is preferable that $R^{A1}$ is RA, further preferable is a compound of the formula (IVa), a compound of the formula (IVb), a compound of the formula (IVg), or a compound of the formula (IVh), and most preferable is a compound of formula (IVa).

In the following step to obtain a compound of the formula (IV) from a compound of the formula (III) or (VI), if the compound of the formula (IV) has (R)-configuration around the carbon atom attached with a dashed wedge line to hydrogen, the compound of the formula (III) or (VI) may have (R)- or (S)-configuration around the carbon atom to which RA is bonded, provided that desired steric configuration around the carbon atom to which RA is bonded should depend on the type of RA group, the position of RA or the condition of the intramolecular cyclization reaction.

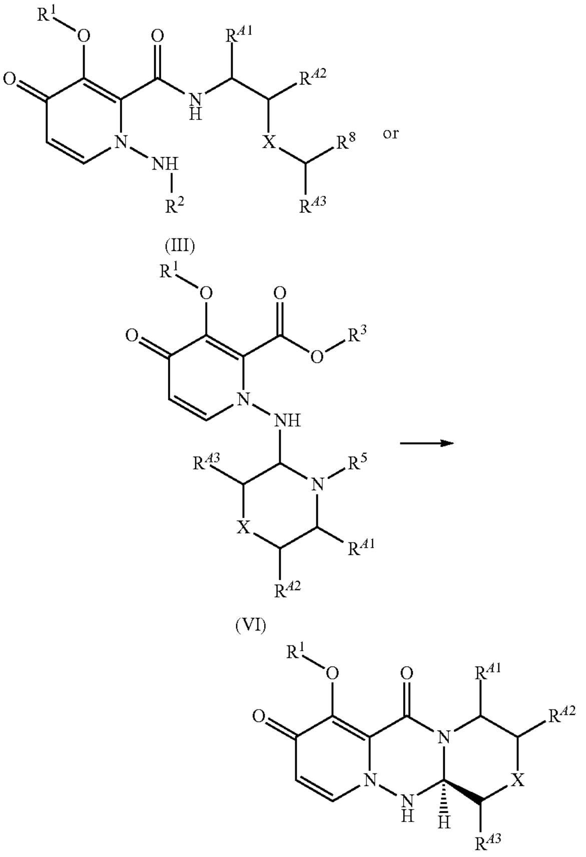

or (III)

(VI)

(IV)

For example, a compound of the formula (IV) having (S)-configuration around the carbon atom attached with a dashed wedge line to hydrogen may be obtained by intramolecular cyclization reaction using a compound of the formula (III) or (VI) having (R)-configuration around the carbon atom to which RA is bonded. If so, a compound of the formula (IV) having (R)-configuration around the carbon atom attached with a dashed wedge line to hydrogen could be obtained by intramolecular cyclization reaction using a compound of the formula (III) or (VI) having (5)-configuration around the carbon atom to which RA is bonded.

Alternatively, a compound of the formula (IV) having (S)-configuration around the carbon atom attached with a dashed wedge line to hydrogen may be obtained by intramolecular cyclization reaction using a compound of the formula (III) or (VI) having (S)-configuration around the carbon atom to which RA is bonded. If so, a compound of the formula (IV) having (R)-configuration around the carbon atom attached with a dashed wedge line to hydrogen could be obtained by intramolecular cyclization reaction using a compound of the formula (III) or (VI) having (R)-configuration around the carbon atom to which RA is bonded.

Examples of such step include, but not limited to, the followings:

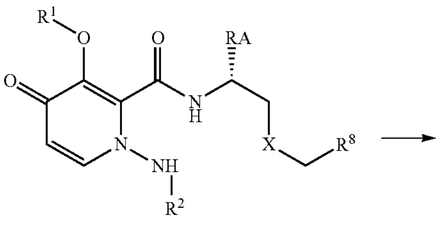

(III')

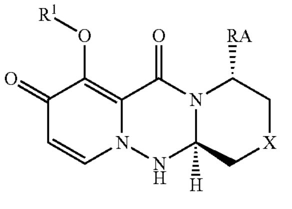

(IV')

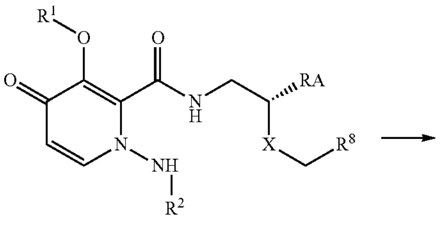

(III")

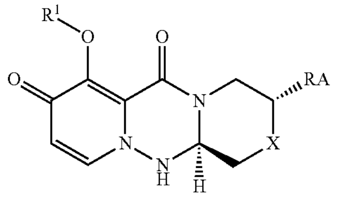

(IV")

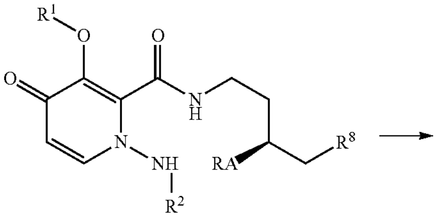

(IIIm)

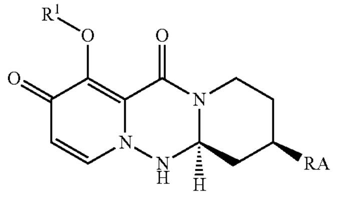

(IVm)

Preferred embodiments for each substituent and for the reaction conditions in each process are described below. The possible combinations of the following embodiments are preferable.

A preferred embodiment for $R^1$ is benzyl or alkyl and alkyl is preferable.

A preferred embodiment for $R^2$ is t-butyldimethylsilyl, t-butoxycarbonyl, or benzyloxycarbonyl, and t-butoxycarbonyl is preferable.

A preferred embodiment for $R^3$ is alkyl or haloalkyl.

A preferred embodiment for $R^4$ is hydrogen or alkyl.

A preferred embodiment for $R^5$ is hydrogen, Alloc or Fmoc.

A preferred embodiment for $R^6$ is alkyl.

A preferred embodiment for $R^7$ is $NH_2$ or NHBoc.

A preferred embodiment for $R^8$ is —CHO or —CH($OR^4$)($OR^4$) wherein $R^4$ is hydrogen or alkyl.

A preferred embodiment for RA is optionally protected carboxy, silyl-type functional group, and optionally protected carboxy is preferable.

A preferred embodiment for $R^{1a}$ is alkyl.

A preferred embodiment for $R^{1b}$ is benzyl or alkyl.

A preferred embodiment for $R^{1c}$ is benzyl or alkyl.

A preferred embodiment for $R^{3a}$ is hydrogen.

A preferred embodiment for $R^B$ is alkyl.

A preferred embodiment for $R^C$ is alkyl.

A preferred embodiment for $R^D$ is alkyloxy or dialkylamino.

A preferred embodiment for Z1 is chloro, bromo or iodo.

A preferred embodiment for Z2 is hydrogen, halogen or alkyloxy.

General procedures of the process of the present invention are represented by the following schemes. As used herein, "solid wedge line" and "dashed wedge line" indicate absolute configuration.

In a reaction of a compound with another compound, as described herein, these compounds may be a salt or a solvate thereof. Moreover, the reactions as described below may be conducted "in continuous steps" without isolation. Conducting "in continuous steps" comprises performing the next step without isolation of a compound obtained by the reaction in the preceding step. For example, two steps may be carried out in one-pot.

A compound of the formula (VIII) or (IX) can be used as a medicament in a form of a salt. Examples of such pharmaceutically acceptable salt of the compound of the formula (VIII) or (IX) include salts with alkaline metals (e.g., lithium, sodium, potassium), alkaline earth metals (e.g., calcium, barium), magnesium, transition metals (e.g., zinc, iron), ammonia, organic bases (e.g., trimethylamine, triethylamine, dicyclohexylamine, ethanolamine, diethanolamine, triethanolamine, meglumine, ethylenediamine, pyridine, picoline, quinoline) or amino acids, or salts with inorganic acids (e.g., hydrochloric acid, sulfuric acid, nitric acid, carbonic acid, hydrobromic acid, phosphoric acid, hydroiodic acid), or organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid), particularly, salts with hydrochloric acid, sulfuric acid, phosphoric acid, tartaric acid, methanesulfonic acid and the like. These salts can be formed in accordance with the conventional methods.

The meaning of each term is as follows.

ABCN: 1,1'-azobis(cyclohexanecarbonitrile)

acac: acetylacetonate

AIBN: azobisisobutyronitrile

Alloc: allyloxycarbonyl

AZADO: 2-azaadamantan-N-oxyl

Boc: tert-butoxycarbonyl

COD: 1,5-cyclooctadiene

CPME: cyclopentyl methyl ether

DABCO: 1,4-diazabicyclo[2.2.2]octane dba: dibenzylideneacetone

DBDMH: 1,3-dibromo-5,5-dimethylhydantoin
DBU: diazabicycloundecene
DDDS: 4,4'-dichlorodiphenyl disulfide
DMA: N,N-dimethylacetamide
DME: dimethoxyethane
DMF: N,N-dimethylformamide
EDC: 1-ethyl-3-(3-dimethylaminopropyl)carbodiimide
$Et_2O$: diethylether
Fmoc: 9-fluorenylmethyloxycarbonyl
HATU: O-(7-azabenzotriazol-1-yl)-N,N,N',N'-tetramethyluronium hexafluorophosphate
HF: hydrogen fluoride
HOBt: 1-hydroxybenzotriazole
MTBE: methyl tert-butyl ether
n-Hex: n-hexyl
NaH: sodium hydride
NBS: N-bromosuccinimide
NCS: N-chlorosuccinimide
NIS: N-iodosuccinimide
NMP: N-methyl-2-pyrrolidone
TBABr: tetrabutylammonium bromide
TBACl: tetrabutylammonium chloride
TBAF: tetrabutylammonium fluoride
TBAOAc: tetrabutylammonium acetate
TFA: trifluoroacetic acid
TEMPO: 2,2,6,6-tetramethylpiperidin-1-oxyl
TEMPOL: 4-hydroxy-2,2,6,6-tetramethylpiperidin-1-oxyl
THF: tetrahydrofuran
T3P: Propylphosphonic anhydride (cyclic trimer)
V-70: 2,2'-azobis(4-methoxy-2,4-dimethylvaleronitrile)
WSCD·HCl: 1-Ethyl-3-(3-dimethylaminopropyl)carbodiimide hydrochloride Scheme 1

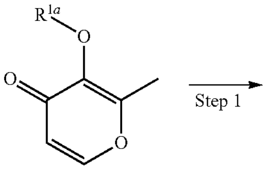

(X)

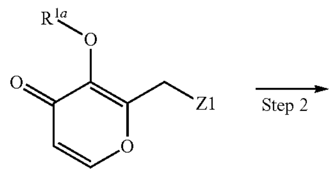

(X1)

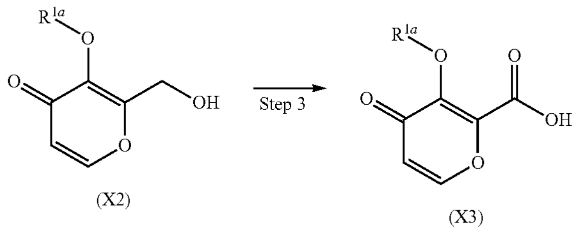

(X2) (X3)

wherein each symbol is as defined above.

Step 1

In this step, a compound of the formula (X) is reacted with a halogenating agent to give a compound of the formula (X1).

The compound of the formula (X1) can be obtained by reacting the compound of the formula (X) with a halogenating agent in the presence of a radical initiator.

Examples of the radical initiator include AIBN, ABCN, V-70, triethylborane, diethylzinc and the like, preferably AIBN.

Examples of the halogenating agent include NCS, NBS, NIS, chlorine, bromine, iodine, DBDMH and the like, preferably NBS. The reaction may be carried out in an amount of 1.0 to 3.0 molar equivalents, preferably 1.0 to 2.2 molar equivalents, based on the compound of the formula (X).

The solvent is not limited so long as it allows this step to proceed efficiently. Examples include ethyl acetate, acetonitrile, carbon tetrachloride, dichloromethane, THF, DMF, DMA and the like. The reaction can be carried out in a single solvent, in a mixed solvent, or without solvent. Preferred solvent includes ethyl acetate, acetonitrile and carbon tetrachloride.

The reaction temperature may be, but not limited to, about 0 to 100° C., preferably room temperature to 90° C.

The reaction time may be, but not limited to, 0.5 to 24 hours, preferably 1 to 12 hours.

Step 2

In this step, a compound of the formula (X1) is subjected to nucleophilic substitution with hydroxide ion to give a compound of the formula (X2).

The compound of the formula (X2) can be obtained by reacting the compound of the formula (X1) with hydroxide ion in the presence of a base.

Examples of the base include sodium carbonate, potassium carbonate, calcium carbonate, sodium hydroxide, potassium hydroxide, calcium hydroxide and the like, preferably calcium carbonate. The reaction may be carried out in an amount of 1.0 to 10 molar equivalents, preferably 2.0 to 5.0 molar equivalents, based on the compound of the formula (X1).

The solvent is not limited so long as it allows this step to proceed efficiently. Examples include acetonitrile, dioxane, water, dichloromethane, THF, DMF, DMA, DME and the like. The reaction can be carried out in a single solvent, in a mixed solvent, or without solvent. Preferred solvent includes a mixture of acetonitrile and water and a mixture of dioxane and water.

The reaction temperature may be, but not limited to, room temperature to 150° C., preferably room temperature to 100° C.

The reaction time may be, but not limited to, 0.5 to 24 hours, preferably 1 to 12 hours.

Step 3

In this step, a compound of the formula (X2) is oxidized to give a compound of the formula (X3).

The compound of the formula (X3) can be obtained by reacting the compound of the formula (X2) with a radical initiator and an oxidizing agent in the presence of a base.

Examples of the base include sodium hydrogen carbonate, sodium carbonate, sodium hydroxide, potassium carbonate, calcium carbonate and the like, preferably sodium hydrogen carbonate. The reaction may be carried out in an amount of 1.0 to 2.0 molar equivalents, preferably 1.0 to 1.2 molar equivalents, based on the compound of the formula (X2).

Examples of the radical initiator include TEMPO, AZADO, TEMPOL and the like, preferably TEMPO.

Examples of the oxidizing agent include sodium chlorite, sodium hypochlorite, tert-butyloxychloride, NCS, metachloroperbenzoic acid and the like, preferably sodium hypochlorite. The reaction may be carried out in an amount of 2.0 to 5.0 molar equivalents, preferably 2.2 to 2.5 molar equivalents, based on the compound of the formula (X2).

The solvent is not limited so long as it allows this step to proceed efficiently. Examples include acetonitrile, water, dichloromethane, THF, DMF, DMA and the like. The reaction can be carried out in a single solvent, in a mixed solvent, or without solvent. Preferred solvent includes a mixture of dichloromethane and water and a mixture of acetonitrile and water.

The reaction temperature may be, but not limited to, about 0 to 100° C., preferably 0° C. to room temperature.

The reaction time may be, but not limited to, 0.5 to 24 hours, preferably 1 to 12 hours.

Scheme 2

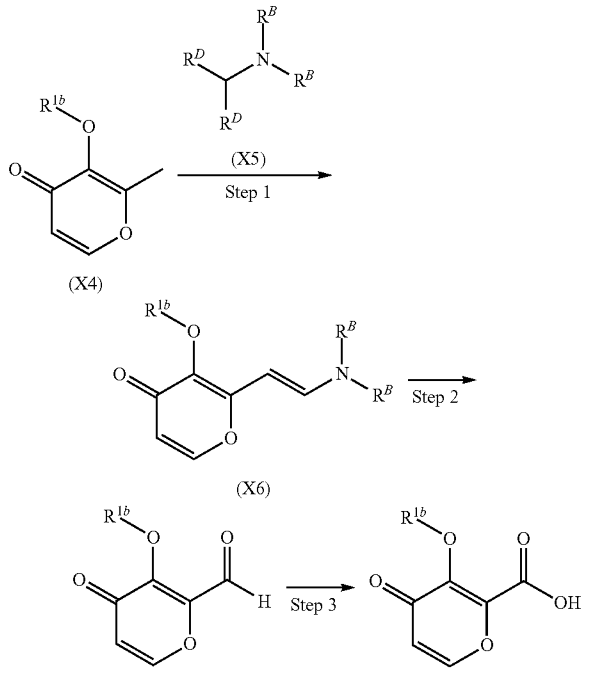

(X4)

(X6)

(X7) (X8)

wherein each symbol is as defined above.

Step 1

In this step, a compound of the formula (X4) is converted to an enamine by reacting with a compound of the formula (X5) or (X5') to give a compound of the formula (X6).

The compound of the formula (X6) can be obtained by reacting the compound of the formula (X4) with the compound of the formula (X5) or (X5') in the presence of an additive agent.

Examples of the compound of the formula (X5) or (X5') include DMF-dimethyl acetal, DMF-diethyl acetal, Brederick reagent, DMF-dimethyl sulfate adduct and the like, preferably DMF-dimethyl acetal. The reaction may be carried out in an amount of 1.0 to 10 molar equivalents, preferably 4.0 to 6.0 molar equivalents, based on the compound of the formula (X4).

Examples of the additive agent include TBAOAc, TBACl, TBABr, DBU, diazabicyclononene, trimethylglycine, potassium acetate and the like, preferably TBAOAc. The reaction may be carried out in an amount of 0.5 to 3.0 molar equivalents, preferably 1.0 to 1.5 molar equivalents, based on the compound of the formula (X4).

The solvent is not limited so long as it allows this step to proceed efficiently. Examples include DMSO, dichloromethane, THF, DMF, DMA and the like. The reaction can be carried out in a single solvent, in a mixed solvent, or without solvent. Preferred solvent includes DMSO and without solvent.

The reaction temperature may be, but not limited to, about room temperature to 200° C., preferably 80° C. to 150° C.

The reaction time may be, but not limited to, 0.5 to 24 hours, preferably 1 to 12 hours.

Step 2

In this step, a compound of the formula (X6) is oxidatively cleaved to give a compound of the formula (X7).

The compound of the formula (X7) can be obtained by reacting the compound of the formula (X6) with an oxidizing agent in the presence or absence of an acid.

Examples of the oxidizing include sodium periodate, hydrogen peroxide, m-chloroperoxybenzoic acid, potassium permanganate and the like, preferably sodium periodate. The reaction may be carried out in an amount of 1.0 to 3.0 molar equivalents, preferably 1.5 to 2.0 molar equivalents, based on the compound of the formula (X6).

Examples of the acid include copper chloride (I) and the like.

The solvent is not limited so long as it allows this step to proceed efficiently. Examples include acetonitrile, water, dichloromethane, THF, DMF, DMA and the like. The reaction can be carried out in a single solvent, in a mixed solvent, or without solvent. Preferred solvent includes a mixture of acetonitrile and water.

The reaction temperature may be, but not limited to, about 0 to 100° C., preferably 0° C. to room temperature.

The reaction time may be, but not limited to, 0.5 to 24 hours, preferably 1 to 12 hours.

Step 3

In this step, a compound of the formula (X7) is oxidized to give a compound of the formula (X8).

The compound of the formula (X8) can be obtained by reacting the compound of the formula (X7) in the same manner as in Step 3 of Scheme 1.

Scheme 3

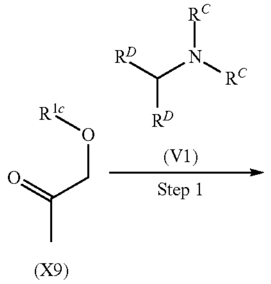

(X9)

-continued

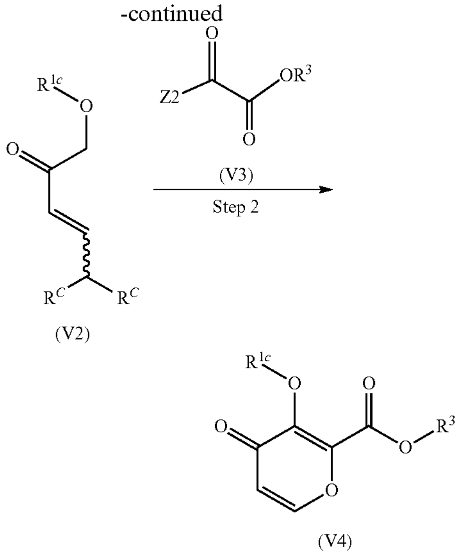

(V2) (V3) (V4)

wherein each symbol is as defined above.

Step 1

In this step, a compound of the formula (X9) is reacted with a compound of the formula (V1) or (V1') to give a compound of the formula (V2).

The compound of the formula (V2) can be obtained by reacting the compound of the formula (X9) with the compound of the formula (V1) or (V1') in the presence of an additive agent.

Examples of the compound of the formula (V1) or (V1') include DMF-dimethyl acetal, DMF-diethyl acetal, Brederick reagent, DMF-dimethyl sulfate adduct and the like, preferably DMF-dimethyl acetal. The reaction may be carried out in an amount of 1.0 to 3.0 molar equivalents, preferably 1.5 to 2.5 molar equivalents, based on the compound of the formula (X9).

Examples of the additive agent include formic acid, acetic acid, oxalic acid, citric acid, trifluoroacetic acid and the like, preferably acetic acid.

The solvent is not limited so long as it allows this step to proceed efficiently. Examples include toluene, DMSO, dichloromethane, THF, DMF, DMA, cyclopentyl methyl ether and the like. The reaction can be carried out in a single solvent, in a mixed solvent, or without solvent. Preferred solvent includes DMSO and DMA.

The reaction temperature may be, but not limited to, about 0 to 100° C., preferably room temperature to 80° C.

The reaction time may be, but not limited to, 0.5 to 48 hours, preferably 12 to 24 hours.

Step 2

In this step, a compound of the formula (V2) is reacted with a compound of the formula (V3) to give a compound of the formula (V4).

The compound of the formula (V4) can be obtained by reacting the compound of the formula (V2) with the compound of the formula (V3) in the presence of a base and then subjecting the obtained compound to intramolecular cyclization in the presence of an acid.

Examples of the compound of the formula (V3) include dimethyl oxalate, diethyl oxalate, oxalyl chloride, monomethyl oxalate chloride, monoethyl oxalate chloride, preferably diethyl oxalate. The reaction may be carried out in an amount of 1.0 to 4.0 molar equivalents, preferably 2.0 to 3.0 molar equivalents, based on the compound of the formula (V2).

Examples of the base include sodium methoxide, sodium ethoxide, sodium t-butoxide, lithium diisopropylamide, lithium hexamethyldisilazide, sodium hexamethyldisilazide, potassium hexamethyldisilazide, DBU, DBN and the like, and preferably, sodium ethoxide.

The solvent for the reaction with the compound of the formula (V3) is not limited so long as it allows this step to proceed efficiently. Examples include toluene, dichloromethane, THF, DMF, DMA and the like. The reaction can be carried out in a single solvent, in a mixed solvent, or without solvent. Preferred solvent includes toluene.

The reaction temperature for the reaction with the compound of the formula (V3) may be, but not limited to, about 0 to 100° C., preferably 0° C. to room temperature.

The reaction time for the reaction with the compound of the formula (V3) may be, but not limited to, 0.5 to 24 hours, preferably 1 to 12 hours.

Examples of the acid include p-toluenesulfonic acid, methanesulfonic acid, trifluoroacetic acid, pyridinium p-toluenesulfonate and the like, preferably pyridinium p-toluenesulfonate.

The solvent for the intramolecular cyclization reaction is not limited so long as it allows this step to proceed efficiently. Examples include dichloromethane, THF, DMF, DMA, 1,3-dimethyl-2-imidazolidinone, N-methyl-2-pyrrolidone and the like. The reaction can be carried out in a single solvent, in a mixed solvent, or without solvent. Preferred solvent includes DMA, DMF, 1,3-dimethyl-2-imidazolidinone and N-methyl-2-pyrrolidone.

The reaction temperature for the intramolecular cyclization reaction may be, but not limited to, about 0 to 100° C., preferably room temperature to 70° C.

The reaction time for the intramolecular cyclization reaction may be, but not limited to, 0.5 to 24 hours, preferably 0.5 to 4 hours.

Scheme 4

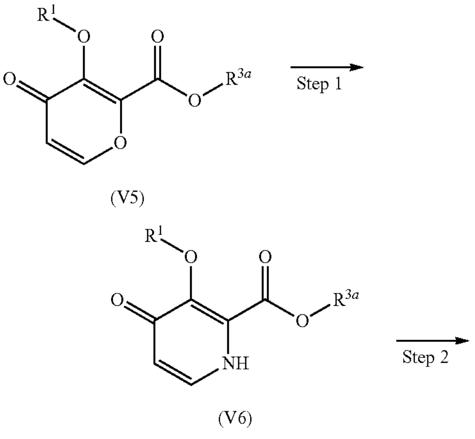

(V5) (V6)

-continued

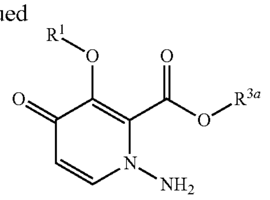

(V7)

wherein each symbol is as defined above.

Step 1

In this step, a compound of the formula (V5) is reacted with ammonia to give a compound of the formula (V6).

The compound of the formula (V6) can be obtained by reacting the compound of the formula (V5) with ammonia.

Examples of ammonia include ammonia water, ammonium carbonate and ammonium acetate, preferably ammonium acetate. The reaction may be carried out in an amount of 1.0 to 10.0 molar equivalents, preferably 6.0 to 10.0 molar equivalents, based on the compound of the formula (v5).

The solvent is not limited so long as it allows this step to proceed efficiently. Examples include water, methanol, ethanol, normal propanol, isopropanol, butanol, isobutanol, tert-butanol, tert-amyl alcohol, ethyl acetate, acetonitrile, carbon tetrachloride, dichloromethane, THF, MTBE, CPME, DMF, DMA, NMP and the like. The reaction can be carried out in a single solvent, in a mixed solvent, or without solvent. Preferred solvent includes water, normal propanol, isobutanol and NMP.

The reaction temperature may be, but not limited to, generally about 0 to 100° C., preferably room temperature to 90° C.

The reaction time may be, but not limited to, generally 0.5 to 24 hours, preferably 1 to 12 hours.

Step 2

In this step, a compound of the formula (V6) is reacted with a hydroxylamine derivative to give a compound of the formula (V7).

The compound of the formula (V7) can be obtained by reacting the compound of the formula (V6) with the hydroxylamine derivative in the presence of a base.

Examples of the hydroxylamine derivative include hydroxylamine-O-sulfonic acid and O-(2,4-dinitrophenyl) hydroxylamine, preferably hydroxylamine-O-sulfonic acid. The reaction may be carried out in an amount of 1.0 to 3.0 molar equivalents, preferably 2.0 to 2.5 molar equivalents, based on the compound of the formula (V6).

Examples of the base include sodium carbonate, potassium carbonate, calcium carbonate, cesium carbonate, sodium hydroxide, lithium hydroxide, potassium hydroxide, calcium hydroxide, DBU, tetramethylguanidine, tripotassium phosphate, trisodium phosphate, and the like, preferably potassium carbonate, cesium carbonate, potassium hydroxide. The reaction may be carried out in an amount of 3.0 to 10 molar equivalents, preferably 5.0 to 8.0 molar equivalents, based on the compound of the formula (V6).

The solvent is not limited so long as it allows this step to proceed efficiently. Examples include water, methanol, ethanol, normal propanol, isopropanol, butanol, isobutanol, tert-butanol, tert-amyl alcohol, ethyl acetate, acetonitrile, carbon tetrachloride, dichloromethane, THF, MTBE, CPME, DMF, DMA, NMP and the like. The reaction can be carried out in a single solvent, in a mixed solvent, or without solvent. Preferred solvent may be water, tert-amyl alcohol, or the like.

The reaction temperature may be, but not limited to, generally about 0 to 100° C., preferably room temperature to 40° C.

The reaction time may be, but not limited to, generally 0.5 to 24 hours, preferably 1 to 12 hours.

Scheme 5

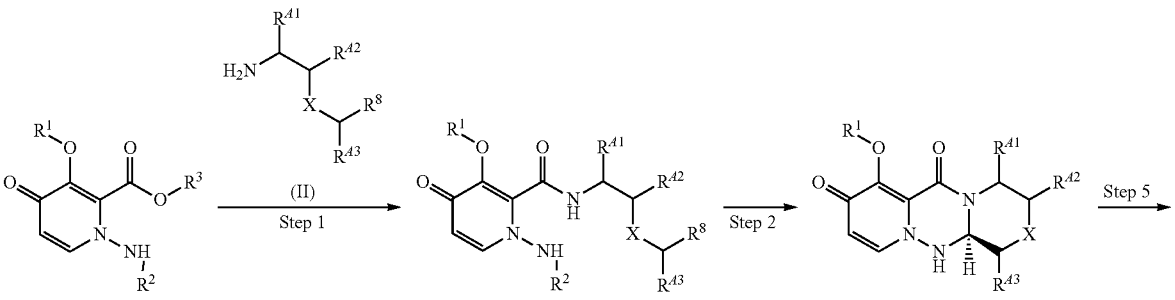

(I) (II) (III) (IV)

(Ia): $R^3$ = H (Ib): $R^2$ = H

-continued

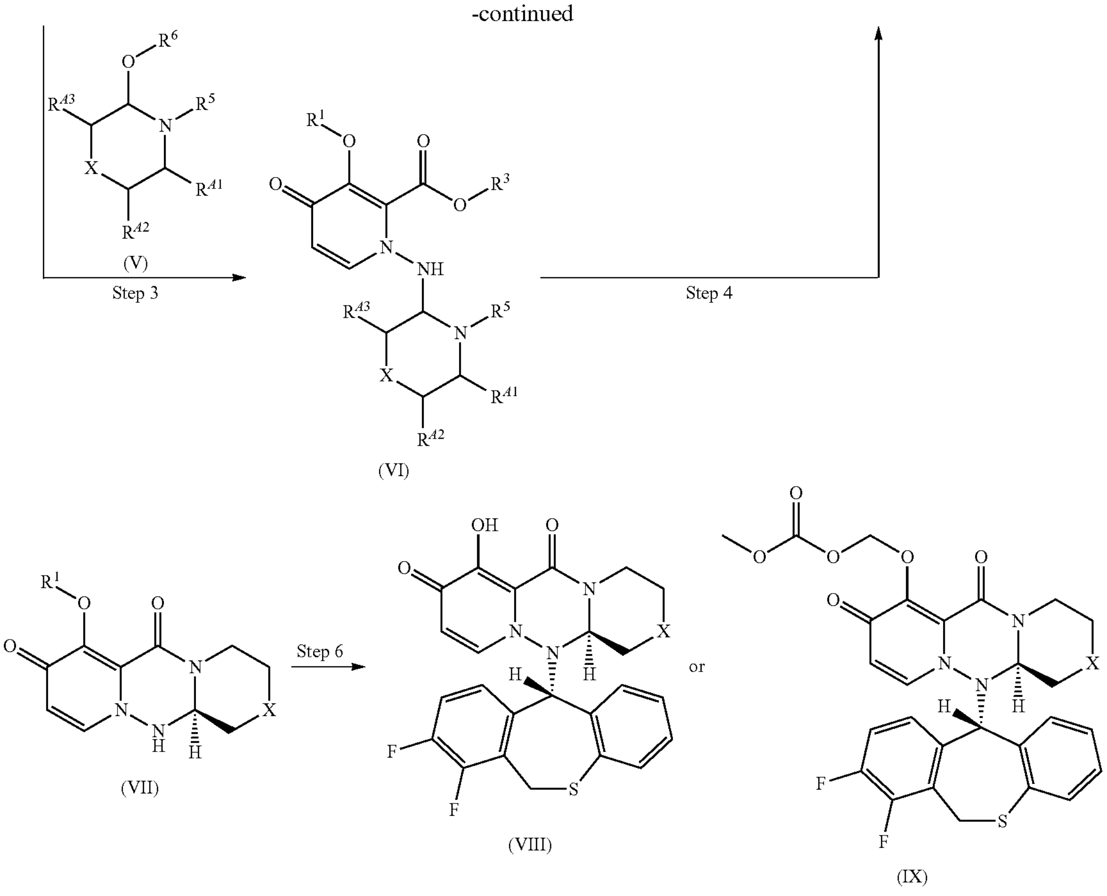

(V) (VI) (VII) (VIII) or (IX)

wherein each symbol is as defined above.

Step 1

In this step, a compound of the formula (Ia) is reacted with a compound of the formula (II) to give a compound of the formula (III).

The protecting group for carboxy group of the compound of the formula (I) can be removed to give the compound of the formula (Ia). The deprotection reaction can be carried out by a conventional method as described in Protective Groups in Organic Synthesis, Theodora W Green (John Wiley & Sons). Thereafter, the obtained compound of the formula (Ia) is reacted with an amine of the formula (II) using a condensing agent in the presence or absence of a base to give a compound of the formula (III).

Examples of the base include triethylamine and diisopropylethylamine.

The solvent is not limited so long as it allows this step to proceed efficiently. Examples include dichloromethane, THF, DMF and DMA. The reaction can be carried out in a single solvent, in a mixed solvent, or without solvent. Preferred solvent includes dichloromethane.

Examples of the condensing agent include dicyclohexylcarbodiimide, carbonyldiimidazole, dicyclohexylcarbodiimide-N-hydroxybenzotriazole, EDC, 4-(4,6-dimethoxy-1,3,5-triazin-2-yl)-4-methylmorpholinium chloride, HATU and WSCD·HCl. The condensing agent may be used in an amount of 1 to 5 molar equivalents, preferably 1 to 2 molar equivalents, based on the compound of the formula (Ia).

The reaction temperature may be, but not limited to, about 0 to 100° C., preferably 0° C. to room temperature.

The reaction time may be, but not limited to, 0.5 to 24 hours, preferably 1 to 12 hours.

The above step is carried out under conditions, which are selected appropriately so that RA should not be removed and not be reacted with another functional group.

Step 2

In this step, a compound of the formula (III) is subjected to intramolecular cyclization to give a compound of the formula (IV).

For example, the compound of the formula (III) is subjected to intramolecular cyclization in the presence of an acid to give a compound of the formula (IV).

The solvent is not limited so long as it allows this step to proceed efficiently. Examples include acetonitrile, toluene and THF, which may be used alone or in combination. Preferred solvent includes acetonitrile.

Examples of the acid include methanesulfonic acid, p-toluenesulfonic acid, camphorsulfonic acid, acetic acid and trifluoroacetic acid, which may be used alone or in combination. Preferred acid includes methanesulfonic acid. The acid may be used in an amount of 1 to 5 molar equivalents, preferably 1 to 3 molar equivalents, based on the compound of the formula (III).

The reaction temperature may be, but not limited to, about 0 to 100° C., preferably room temperature to 80° C.

The reaction time may be, but not limited to, 1 to 24 hours, preferably 1 to 12 hours.

The above step is carried out under conditions, which are selected appropriately so that RA should not be removed and not be reacted with another functional group.

Step 3

In this step, a compound of the formula (Ib) is reacted with a compound of the formula (V) to give a compound of the formula (VI).

The protecting group for amino group of the compound of the formula (I) can be removed to give the compound of the formula (Ib). The deprotection reaction can be carried out by a conventional method as described in Protective Groups in Organic Synthesis, Theodora W Green (John Wiley & Sons). Thereafter, the obtained compound of the formula (Ib) is reacted with a compound of the formula (V) in the presence of an acid to give a compound of the formula (VI).

Examples of the acid include Lewis acids such as boron trifluoride, tin tetrachloride, and zinc chloride, and bronsted acid such as methanesulfonic acid, p-toluenesulfonic acid, camphorsulfonic acid, acetic acid and trifluoroacetic acid. Preferred acids include boron trifluoride and tin tetrachloride.

The solvent is not limited so long as it allows this step to proceed efficiently. Examples include acetonitrile, toluene and THF, which may be used alone or in combination. Preferred solvent includes acetonitrile.

The reaction temperature may be, but not limited to, about −80° C. to room temperature, preferably −40 to 0° C.

The reaction time may be, but not limited to, 0.1 to 24 hours, preferably 0.25 to 2 hours.

The above step is carried out under conditions, which are selected appropriately so that RA should not be removed and not be reacted with another functional group.

Step 4

In this step, a compound of the formula (VI) is subjected to intramolecular cyclization to give a compound of the formula (IV).

The compound of the formula (VI) may be subjected to intramolecular cyclization in the presence of a base, using a Pd catalyst if necessary, to give the compound represented by the formula (IV).

The solvent is not limited so long as it allows this step to proceed efficiently. Examples include acetonitrile, toluene and THF, which may be used alone or in combination. Preferred solvent include THF.

Examples of the base include morpholine, piperidine and dimedone, which may be used alone or in combination. Preferred base includes morpholine.

Examples of the Pd catalyst include tetrakistriphenylphosphine palladium. The reaction temperature may be, but not limited to, about 0 to 100° C., preferably at 20 to 50° C.

The reaction time may be, but not limited to, 0.1 to 24 hours, preferably 1 to 4 hours.

The above step is carried out under conditions, which are selected appropriately so that RA should not be removed and not be reacted with another functional group.

Step 5

In this step, RA group is removed from a compound of the formula (IV) to give a compound of the formula (VII).

Step 5-1 (RA=Optionally Protected Carboxy)

When RA is optionally protected carboxy, a protecting group for carboxy can be removed from the compound of the formula (IV) under a conventional condition for deprotection to give a corresponding carboxy acid. If the RA is carboxy, the carboxylic acid of the formula (IV) can be used as it is. The deprotection reaction can be carried out according to a conventional method as described in Protective Groups in Organic Synthesis, Theodora W Green (John Wiley & Sons). The carboxylic acid is reacted using a photocatalyst and disulfide under light irradiation in the presence of a base to give a compound of the formula (VII).

The solvent is not limited so long as it allows this step to proceed efficiently. Examples include methanol, ethanol, water, dichloromethane and dichloroethane, which may be used alone or in combination. Preferred solvent include a mixture of methanol and water.

Examples of the base include 2,6-lutidine, pyridine, DBU, diisopropylethylamine, triethylamine, N-methylimidazole, imidazole and DABCO. Preferred base includes 2,6-lutidine.

Examples of the photocatalyst include acridinium salt. The acridinium salt is not limited so long as it allows the reaction under light irradiation to proceed efficiently. Preferred examples include 9-mesityl 10-alkyl acridinium salt and 9-mesityl 10-aromatic carbocyclylacridinium salt. Preferred examples include 9-mesityl-2,7-dimethyl 10-methyl acridinium salt and 9-mesityl 10-methylacridinium salt.

Disulfide is a compound having a disulfide group as a functional group. Examples include di(aromatic carbocyclyl) disulfide. Preferred disulfides include diphenyl disulfide and 4,4'-dichlorodiphenyl disulfide.

Examples of the light include blue LED.

The reaction temperature may be, but not limited to, about 0 to 50° C., preferably room temperature.

The reaction time may be, but not limited to, 0.5 to 48 hours, preferably 1 to 24 hours.

Step 5-2 (RA=Optionally Protected Carboxy)

The carboxylic acid can be obtained in the same manner as in Step 5-1. The carboxylic acid may be reacted with a N-hydroxy compound etc. using a condensing agent in the presence or absence of a base to give an active ester.

Examples of the base include triethylamine, diisopropylethylamine and DABCO.

The solvent is not limited so long as it allows the step to proceed efficiently.

Examples include dichloromethane, THF, DMF and DMA. The reaction can be carried out in a single solvent, in a mixed solvent, or without solvent. Preferred solvent includes dichloromethane.

Examples of the condensing agent include dicyclohexylcarbodiimide, carbonyldiimidazole, dicyclohexylcarbodiimide-N-hydroxybenzotriazole, EDC, WSCD·HCl, 4-(4,6-dimethoxy-1,3,5-triazin-2-yl)-4-methylmorpholinium chloride, HATU and T3P, which may be used in an amount of 1 to 5 molar equivalents, preferably 1 to 2 molar equivalents, based on the compound (IV).

The reaction temperature may be, but not limited to, about 0 to 100° C., preferably 0° C. to room temperature.

The reaction time may be, but not limited to, 0.5 to 24 hours, preferably 1 to 12 hours.

The obtained active ester is decarboxylated using a metal catalyst, a ligand and a reducing agent to give a compound of the formula (VII).

Examples of the metal catalyst include a nickel catalyst, a palladium catalyst, a copper catalyst, a cobalt catalyst and an iron catalyst such as $NiCl_2$, $NiBr_2$, $NiI_2$, $Ni(COD)_2$, $Ni(acac)_2$, $Pd_2(dba)_3$, $PdCl_2$, $Pd(OAc)_2$, CuCl, CuBr, CuI, $CuCl_2$, $CuBr_2$, $CuI_2$, Cu(OAc), $Cu(OAc)_2$, $Co(acac)_2$, $Co(acac)_3$, $CoCl_2$, $CoBr_2$, $CoI_2$, $Fe(OAc)_2$, $Fe(acac)_2$, $Fe(acac)_3$, $FeCl_2$, $FeBr_2$, $FeI_2$, and the like. Preferred metal catalyst include $NiCl_2 \cdot 5H_2O$.

Examples of the ligand include $PPh_3$, Xantphos and 2,2'-bipyridine derivatives. The 2,2'-bipyridine derivative is not limited so long as it allows to work as a bipyridine ligand. Examples include 4,4'-dimethyl-[2,2']bipyridine, 4,4'-diethyl-[2,2']bipyridine, 4,4'-dinonyl-[2,2']bipyridine, 4,4'-dicyano-2,2'-bipyridine, 2,2'-bipyridine-4,4'-dicarboxylic acid, dimethyl 2,2'-bipyridine-4,4'-dicarboxylate, 2,2'-bipyridine-4,4'-dicarboxamide, 4,4'-bis(hydroxymethyl)-2,2'-bipyridine, 4,4'-bis(bromomethyl)-2,2'-bipyridine, tetraethyl 2,2'-bipyridine-4,4'-diylbis(methylene)diphosphonate, (E/Z)-4,4'-distyryl-2,2'-bipyridine, 4,4'-dimethoxy-2,2'-bipyridine, diisobutyl 2,2'-bipyridine-4,4'-dicarboxylate, 4,4'-di-tert-butyl-2,2'-bipyridine, and the like. Preferred ligand includes 4,4'-di-tert-butyl-2,2'-bipyridine.

The solvent is not limited so long as it allows the step to proceed efficiently. Examples include DMF, DMA, THF, isopropyl alcohol and dichloromethane. The reaction can be carried out in a single solvent, in a mixed solvent, or without solvent. Preferred solvent includes a mixture of DMF, THF and isopropyl alcohol.

Examples of the reducing agent include zinc, manganese, phenylsilane, triethylsilane, chlorosilane and mixtures thereof. Preferred reducing agent includes a mixture of zinc and phenylsilane.

The reaction temperature may be, but not limited to, about 0 to 100° C., preferably room temperature to 80° C.

The reaction time may be, but not limited to, 0.5 to 24 hours, preferably 1 to 12 hours.

The obtained active ester is decarboxylated using thiol or other reducing agent in the presence or absence of a radical initiator to give a compound of the formula (VII).

Thiol is a compound having a hydrogenated sulfur at the terminal. Examples include alkylthiol optionally substituted by a group selected from Substituent Group C and aromatic carbocyclylthiol optionally substituted by a group selected from Substituent Group D. Preferred thiol includes t-nonanethiol.

Examples of the other reducing agent include tin hydride and tris-(trimethylsilyl)silane.

Examples of the radical initiator include AIBN, ABCN, V-70, triethylborane and diethylzinc. Preferred radical initiator includes AIBN.

The solvent is not limited so long as it allows the step to proceed efficiently. Examples include DMF, DMA, THF, isopropyl alcohol and dichloromethane. The reaction can be carried out in a single solvent, in a mixed solvent, or without solvent. Preferred solvent includes DMA.

The reaction temperature may be, but not limited to, about 0 to 100° C., preferably room temperature to 80° C.

The reaction time may be, but not limited to, 0.5 to 24 hours, preferably 1 to 12 hours.

Step 5-3 (RA=Silyl-Type Functional Group)

The compound of the formula (IV) is reacted with a fluoride ion reagent to give the compound of the formula (VII).

Examples of the fluoride ion reagent include TBAF, HF·pyridine, HF·triethylamine. Preferred fluoride ion reagent includes TBAF.

The solvent is not limited so long as it allows the step to proceed efficiently. Examples include DMF, DMA, THF, dichloromethane and ethyl acetate. The reaction can be carried out in a single solvent, in a mixed solvent, or without solvent. Preferred solvents include THF and dichloromethane.

The reaction temperature may be, but not limited to, about 0 to 100° C., preferably 0° C. to room temperature.

The reaction time may be, but not limited to, 0.5 to 24 hours, preferably 1 to 12 hours.

Step 5-4(1) (RA=Optionally Protected Amino)

The protecting group for amino group is removed from a compound of the formula (IV) under a conventional condition for deprotection. The obtained amine is diazotizated and then reduced to give a compound of the formula (VII).

The deprotection reaction can be carried out by a conventional method as described in Protective Groups in Organic Synthesis, Theodora W Green (John Wiley & Sons).

Examples of the reducing agent include hypophosphorous acid. The solvent is not limited so long as it allows the step to proceed efficiently. Examples include DMF, DMA, THF, dichloromethane and ethyl acetate. The reaction can be carried out in a single solvent, in a mixed solvent, or without solvent. Preferred solvents include THF and dichloromethane.

The reaction temperature may be, but not limited to, about 0 to 100° C., preferably room temperature to 80° C.

The reaction time may be, but not limited to, 0.5 to 24 hours, preferably 1 to 12 hours.

Step 5-4(2) (RA=Optionally Protected Amino)

The protecting group for amino group is removed from a compound of the formula (IV) under a conventional condition for deprotection. The obtained primary amine is converted into isonitrile and then reduced using a reducing agent in the presence or absence of radical initiator to give a compound of the formula (VII).

The deprotection reaction can be carried out by a conventional method as described in Protective Groups in Organic Synthesis, Theodora W Green (John Wiley & Sons).

Examples of the reducing agent include tin hydride, tris(trimethylsilyl) silane and thiol.

Examples of the radical initiator include AIBN, ABCN, V-70, triethylborane and diethylzinc. Preferred radical initiator includes AIBN.

The solvent is not limited so long as it allows the step to proceed efficiently. Examples include DMF, DMA, THF, dichloromethane and ethyl acetate. The reaction can be carried out in a single solvent, in a mixed solvent, or without solvent. Preferred solvents include THF and dichloromethane.

The reaction temperature may be, but not limited to, about 0 to 100° C., preferably room temperature to 80° C.

The reaction time may be, but not limited to, 0.5 to 24 hours, preferably 1 to 12 hours.

Step 5-5 (RA=Chlorine, Bromine or Iodine)

The compound of the formula (IV) is reduced to remove RA group to give a compound of the formula (VII).

Examples of the reduction condition include Pd—C/$H_2$, $NaBH_4$, $LiBH_4$ and LAH. Preferred reduction condition includes Pd—C/$H_2$.

The solvent is not limited so long as it allows the step to proceed efficiently. Examples include DMF, DMA, THF, dichloromethane and ethyl acetate. The reaction can be carried out in a single solvent, in a mixed solvent, or without solvent. Preferred solvents include THF and dichloromethane.

The reaction temperature may be, but not limited to, about 0 to 100° C., preferably 0° C. to room temperature.

The reaction time may be, but not limited to, 0.5 to 24 hours, preferably 1 to 12 hours.

Step 5-6 (RA=Optionally Protected Hydroxy)

The protecting group for hydroxy group is removed from a compound of the formula (IV) under a conventional condition. The hydroxy group of the obtained compound is converted into pseudohalide and then reductively removed to give a compound of the formula (VII). The deprotection reaction can be carried out by a conventional method as described in Protective Groups in Organic Synthesis, Theodora W Green (John Wiley & Sons) and the like.

Examples of the pseudohalide include mesylate, tosylate and triflate. Preferred pseudohalide includes triflate.

The solvent is not limited so long as it allows the step to proceed efficiently. Examples include DMF, DMA, THF, dichloromethane and ethyl acetate. The reaction can be carried out in a single solvent, in a mixed solvent, or without solvent. Preferred solvents include THF and dichloromethane.

The reaction temperature may be, but not limited to, about 0 to 100° C., preferably 0° C. to room temperature.

The reaction time may be, but not limited to, 0.5 to 24 hours, preferably 1 to 12 hours.

Step 6

The compound of the formula (VIII) or (IX) can be obtained according to the method described in any one of Patent Documents 19 to 21.

As used herein, "diastereomer ratio" refers to the ratio of the HPLC area percentage or NMR peak intensity between the two stereoisomers as shown below.

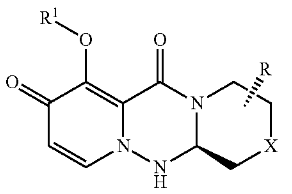

a

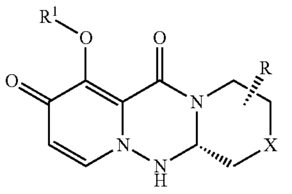

b wherein each symbol is as defined above.

EXAMPLES

The present invention will be explained in more detail below by way of Examples, but the present invention is not limited by them.

The NMR analysis was carried out at 400 MHz, using DMSO-$d_6$ or $CDCl_3$.

RT represents a retention time at LC/MS: liquid chromatography/mass spectrometry, and was measured under the following conditions.

(Measurement Condition)

[1] Column: ACQUITY UPLC (Registered trademark) BEH C18 (1.7 μm i.d.2.1×50 mm) (Waters)
Flow rate: 0.8 mL/min
UV detection wavelength: 254 nm
Mobile phase: [A]: 0.1% formic acid in water, [B]: 0.1% formic acid in acetonitrile
Gradient: a linear gradient of 5% to 100% solvent [B] over 3.5 minutes, and then 100% solvent [B] kept for 0.5 minutes.

Measurement of X-Ray Powder Diffraction Pattern

The powder X-ray diffraction measurement of the crystal obtained in each Example was carried out according to the general test method described in the Japanese Pharmacopoeia. The measurement conditions are as follows.

Apparatus: MinFlex 600 RINT-TTRIII (Rigaku Corporation)
Detector: high-speed one-dimensional detector (D/TecUltra 2) with variable knife edge
Detection mode: reflection
Light source: Cu bulb
Operating Wavelength: CuKα rays
Tube current: 10 mA, or 15 mA
Tube voltage: 30 Kv, or 40 Kv
Sample plate: aluminum or glass
X-ray incidence angle (θ): 3-40°, sampling width: 0.01°, or
X-ray incident angle (θ): 4-40°, sampling width: 0.02°

Generally, the diffraction angles (2θ) in X-ray powder diffraction may contain errors within the range of ±0.2°, and thus, the values of the diffraction angles should be understood to include values within the range of ±0.2°. Therefore, the present invention encompasses crystals having peak diffraction angles that match within an error of ±0.2°, as well as the crystals having peak diffraction angles that completely match in the X-ray powder diffraction.

Also, the data, especially the X-ray intensity, may vary significantly depending on the conditions of the X-ray diffraction measurement, such as loading method of the crystals into the X-ray diffraction apparatus and particle size of the crystals. Thus, the identity of the crystal form of the compound is not denied even if the data do not match in the relative intensity of the peak.

Example 1

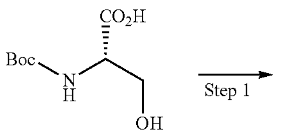

1

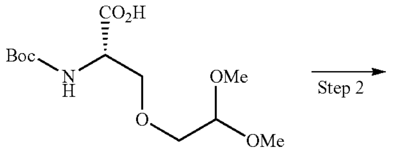

2

-continued

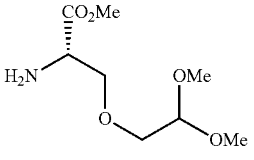

3

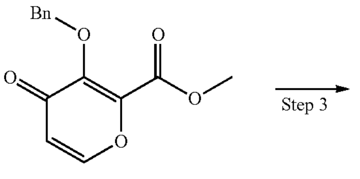

4

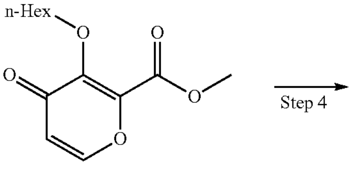

5

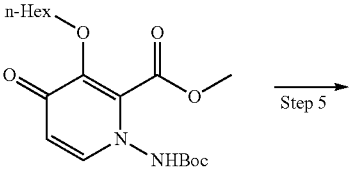

6

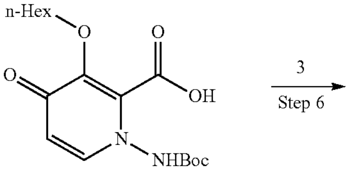

7

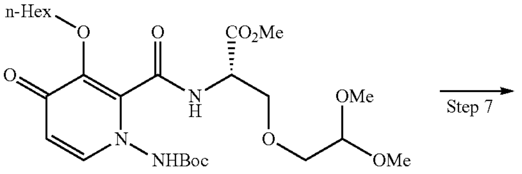

8

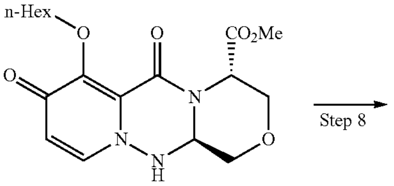

9

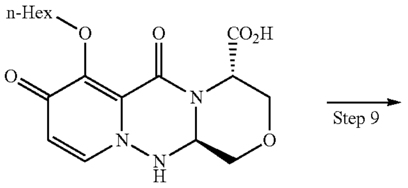

10

-continued

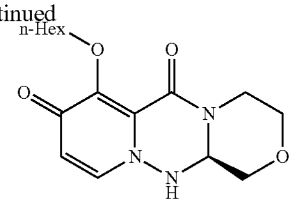

11

Step 1

To a suspension of NaH (3.96 g, 99 mmol) in DMF (36 mL) was added dropwise a solution of Boc-L-serine (9.27 g, 45 mmol) in DMF (45 mL) for 30 minutes with ice-cooling under nitrogen atmosphere, and then added dropwise bromoacetaldehyde dimethylacetal (10.6 mL, 90 mmol) for 10 minutes. The mixture was warmed up to room temperature over 3 hours and was stirred for 5 hours. The mixture was poured into water (90 g) and concentrated. The aqueous layer was washed with $Et_2O$ and the pH was adjusted to 3.3 by adding hydrochloric acid. The aqueous layer was extracted with ethyl acetate (100 mL). The aqueous layer was extracted again with ethyl acetate (100 mL). The organic layers were combined and dried over sodium sulfate and concentrated under reduced pressure to obtain crude Compound 2 (9.52 g).

1H-NMR ($CDCl_3$) δ: 5.54-5.52 (br m, 1H), 4.50 (t, J=5.1 Hz, 1H), 4.44-4.42 (br m, 1H), 4.01-3.99 (br m, 1H), 3.74 (dd, J=9.7, 4.1 Hz, 1H), 3.55 (d, J=5.1 Hz, 2H), 3.39 (s, 6H), 1.47 (s, 9H).

Step 2

To a solution of the crude Compound 2 (9.52 g) in methanol (33 mL) was added methanesulfonic acid (6.32 mL, 97 mmol) at 0° C. under nitrogen atmosphere, and the mixture was stirred at room temperature for 18 hours. The solvent was removed from the mixture under reduced pressure, and the obtained residue was added to an aqueous solution of potassium carbonate at 0° C. The mixture was extracted five times with chloroform (50 mL). The organic layers were combined and washed with brine (20 mL), dried over anhydrous sodium sulfate, and the solvent was removed under reduced pressure to obtain Compound 3 (3.76 g, 40% in 2 steps).

1H-NMR ($CDCl_3$) δ: 4.48 (t, J=5.2 Hz, 1H), 3.80-3.70 (m, 5H), 3.65 (t, J=4.7 Hz, 1H), 3.52 (d, J=5.1 Hz, 2H), 3.39 (s, 6H).

Step 3

To a solution of Compound 4 (3.00 g, 11.5 mmol) in dichloromethane (12 mL) was added TFA (8.88 mL, 13.1 mmol) under nitrogen atmosphere, and the mixture was stirred at room temperature for 18 hours. The mixture was concentrated under reduced pressure, and the obtained solid was treated with a mixed solution of diisopropyl ether and hexane (1:1) and filtered to obtain a deprotected product (1.98 g).

To a solution of the obtained compound (1.98 g, 11.6 mmol) in DMA (40 mL) were added 1-iodohexane (5.15 mL, 35.0 mmol) and DBU (5.26 mL, 35.0 mmol), and the mixture was stirred at room temperature for 18 hours. To the mixture was added 1M aqueous hydrochloric acid, and the mixture was extracted three times with ethyl acetate. The organic layer was washed with water and brine, dried over anhydrous sodium sulfate and concentrated under reduced pressure. The obtained residue was purified by silica gel column chromatography (hexane-ethyl acetate) to obtain Compound 5 (2.42 g, 82%).

LC/MS (ESI): m/z=255 $[M+H]^+$, RT=1.97 min

Step 4

Compound 6 was obtained in the same manner as described in WO2016/175224.

Step 5

To a solution of Compound 6 (3.00 g, 8.14 mmol) in ethanol (7.86 mL) was added 2M aqueous sodium hydroxide (17.8 mL, 35.6 mmol) under nitrogen atmosphere, and the mixture was stirred at 60° C. for 6 hours. To the mixture was added 2M aqueous hydrochloric acid (18 mL), and then added water. The precipitated solid was filtered and washed with water to obtain Compound 7 (2.75 g, 95%).

LC/MS (ESI): m/z=354 $[M+H]^+$, RT=1.24 min

Step 6

To a solution of Compound 3 (494 mg, 2.03 mmol) and Compound 7 (532 mg, 1.50 mmol) in DMF (11 mL) were added HOBt (263 mg, 1.95 mmol) and WSCD HCl (374 mg, 1.95 mmol) at 0° C. under nitrogen atmosphere, and the mixture was stirred at 0° C. for 2 hours and then stirred at room temperature for 1 hour. To the mixture was added water (20 mL), and the mixture was extracted twice with ethyl acetate (30 mL). The organic layer was washed with a saturated aqueous sodium bicarbonate (20 mL) and brine (20 mL). The organic layers were combined and dried over anhydrous sodium sulfate and concentrated under reduced pressure. The obtained residue was purified by silica gel column chromatography (chloroform-methanol) to obtain Compound 8 (777.0 mg, 95%).

$^1$H-NMR ($CDCl_3$) δ: 8.54 (s, 1H), 8.09 (s, 1H), 7.34 (d, J=7.9 Hz, 1H), 6.38 (d, J=7.8 Hz, 1H), 4.77-4.74 (m, 1H), 4.44 (t, J=5.1 Hz, 1H), 4.31-4.18 (m, 2H), 4.04 (dd, J=9.7, 3.5 Hz, 1H), 3.81-3.74 (m, 4H), 3.51 (d, J=5.1 Hz, 2H), 3.36 (d, J=2.1 Hz, 6H), 1.75-1.60 (m, 2H), 1.48 (s, 9H), 1.42-1.25 (m, 6H), 0.88 (t, J=6.8 Hz, 3H).

Step 7

To a solution of Compound 8 (114 mg, 0.21 mmol) in acetonitrile (2.3 mL) were added water (0.46 mL) and methanesulfonic acid (0.041 mL, 0.63 mmol) under nitrogen atmosphere, and the mixture was stirred at 60° C. for 3 hours. To the mixture was added a saturated aqueous sodium bicarbonate (5 mL), and the mixture was extracted three times with chloroform (10 mL). The organic layers were combined and washed with brine (5 mL), dried over anhydrous sodium sulfate and concentrated under reduced pressure. The obtained residue was purified by silica gel column chromatography (chloroform-methanol) to obtain Compound 9 (58.5 mg, 75%).

$^1$H-NMR ($CDCl_3$) δ: 7.36 (d, J=7.7 Hz, 1H), 6.25 (d, J=7.7 Hz, 1H), 5.55 (d, J=13.4 Hz, 1H), 5.00-4.95 (m, 2H), 4.50 (d, J=11.9 Hz, 1H), 4.28-4.23 (m, 1H), 4.14 (dd, J=11.4, 4.7 Hz, 1H), 3.99-3.84 (m, 2H), 3.78 (s, 3H), 3.25 (t, J=10.8 Hz, 1H), 1.78-1.70 (m, 2H), 1.60 (s, 9H), 1.40-1.25 (m, 6H), 0.87 (t, J=6.9 Hz, 3H).

Step 8

To a solution of Compound 9 (100 mg, 0.26 mmol) in methanol (1.0 mL) and THF (0.5 mL) was added 2M aqueous sodium hydroxide (0.26 mL, 0.53 mmol) at 0° C. under nitrogen atmosphere, and the mixture was warmed up to room temperature over 4 hours with stirring. To the mixture was added 1N aqueous hydrochloric acid (0.55 mL), and the mixture was extracted three times with chloroform (10 mL). The organic layers were combined and washed with brine (10 mL), dried over anhydrous sodium sulfate, and the solvent was removed under reduced pressure to obtain Compound 10 (85.3 mg, 89%).

$^1$H-NMR (DMSO-$D_6$) δ: 7.71 (d, J=7.7 Hz, 1H), 7.35 (d, J=12.8 Hz, 1H), 6.21 (d, J=7.7 Hz, 1H), 4.90-4.83 (m, 2H), 4.34 (d, J=11.9 Hz, 1H), 4.07 (dd, J=11.3, 4.6 Hz, 1H), 3.95 (dt, J=21.9, 7.8 Hz, 2H), 3.71 (dd, J=12.0, 3.8 Hz, 1H), 3.17 (t, J=10.9 Hz, 1H), 1.69-1.58 (m, 2H), 1.39-1.23 (m, 6H), 0.86 (t, J=6.8 Hz, 3H).

Step 9

To a mixture of Compound 10 (37 mg, 0.10 mmol), DDDS (2.87 mg, 10 μmol) and 9-mesityl-2,7-dimethyl 10-methyl acridinium salt (0.88 mg, 2.0 μmol) were added methanol (1.8 mL) and water (45 μL, 2.5 mmol) under nitrogen atmosphere. After degassing with nitrogen bubbling for 15 minutes, 2,6-lutidine (2.3 μL, 20 μmol) was added. The mixture was stirred at room temperature under blue LED illumination for 14 hours. The mixture was concentrated under reduced pressure. The obtained residue was purified by silica gel column chromatography (chloroform-methanol) to obtain Compound 11 (29.4 mg, 92%).

Example 2

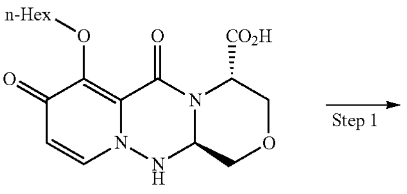

10

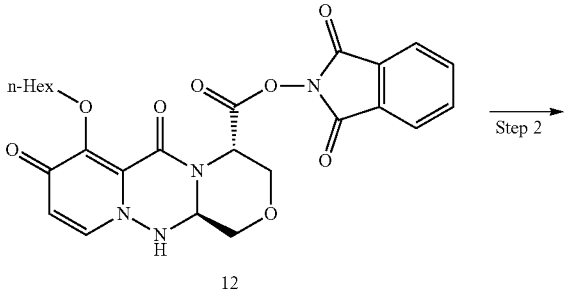

12

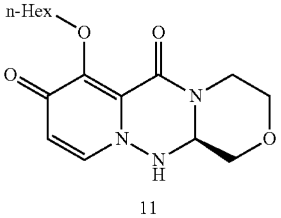

11

Step 1

To a solution of Compound 10 (183 mg, 0.50 mmol) and N-hydroxyphthalimide (163 mg, 1.00 mmol) in dichloromethane (1.8 mL) was added WSCD·HCl (288 mg, 1.50 mmol) at 0° C. under nitrogen atmosphere, and the mixture was stirred at room temperature for 1 hour. To the mixture was added water (10 mL), and the mixture was extracted twice with ethyl acetate (20 mL). The organic layer was washed with brine (10 mL), dried over anhydrous sodium sulfate and the solvent was removed under reduced pressure. The obtained residue was purified by silica gel column chromatography (ethyl acetate) to obtain Compound 12 (203 mg, 80%).

$^1$H-NMR ($CDCl_3$) δ: 7.90-7.79 (m, 4H), 7.35 (d, J=7.7 Hz, 1H), 6.20 (d, J=7.7 Hz, 1H), 5.81 (d, J=13.3 Hz, 1H), 5.41 (d, J=3.5 Hz, 1H), 5.07-5.01 (m, 1H), 4.74 (d, J=12.2 Hz, 1H), 4.28-4.17 (m, 3H), 3.90 (dd, J=16.1, 7.1 Hz, 1H), 3.40 (t, J=10.8 Hz, 1H), 1.80-1.68 (m, 2H), 1.40-1.24 (m, 6H), 0.83 (t, J=6.9 Hz, 3H).

Step 2

To a mixture of Compound 12 (51 mg, 0.10 mmol) and zinc powder (3.27 mg, 50 μmol) were added THF (0.5 mL) and 2-propanol (51 μL) under nitrogen atmosphere. After degassing with nitrogen bubbling for 15 minutes, a solution of nickel chloride hexahydrate (2.4 mg, 10 μmol) and 4,4'-di-tert-butyl-2,2'-bipyridine (5.37 mg, 20 μmol) in DMF (0.1 mL) was added. To the mixture was added phenylsilane (37 μL, 0.3 mmol), and the mixture was stirred at 60° C. for 2 hours. The mixture was concentrated under reduced pressure. The obtained residue was purified by silica gel column chromatography (chloroform-methanol) to obtain Compound 11 (15 mg, 48%).

Example 3

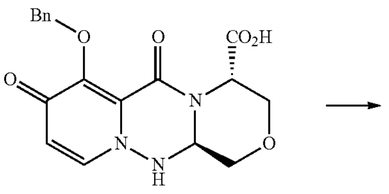

13

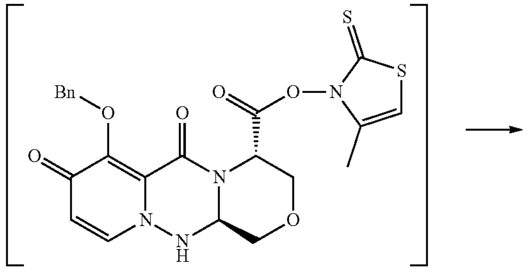

14

-continued

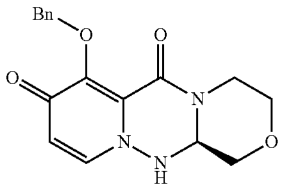

15

To a solution of Compound 13 (37.1 mg, 1.00 mmol), which was synthesized in the same manner as described in Step 1 to Step 8 of Example 1, and 3-hydroxy-4-methylthiazol-2(3H)-thione (22.1 mg, 1.50 mmol) in N-methyl pyrrolidone (0.9 mL) were added DABCO (44.9 mg, 4.00 mmol) and T3P (255 mg, 4.00 mmol) at room temperature under nitrogen atmosphere, and the mixture was stirred at room temperature for 2 hours to obtain a solution of Compound 14. To the mixture was added t-nonanethiol (0.9 mL, 74 mmol) under nitrogen atmosphere, and the mixture was stirred at 55° C. for 2 hours. The mixture was concentrated under reduced pressure. The obtained residue was purified by silica gel column chromatography (chloroform-methanol) to obtain Compound 15 (27 mg, 83%).

$^1$H-NMR (DMSO) δ: 2.80-3.00 (m, 1H), 3.10-3.18 (m, 1H), 3.38-3.50 (m, 1H), 3.98-4.08 (m, 2H), 4.10-4.20 (m, 1H), 4.76-4.84 (m, 1H), 5.04-5.14 (m, 2H), 6.22 (m, J=7.6 Hz, 1H), 7.27-7.40 (m, 4H), 7.56-7.60 (m, 2H), 7.70 (d, J=7.6 Hz, 1H).

Example 4

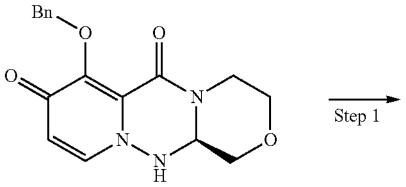

15

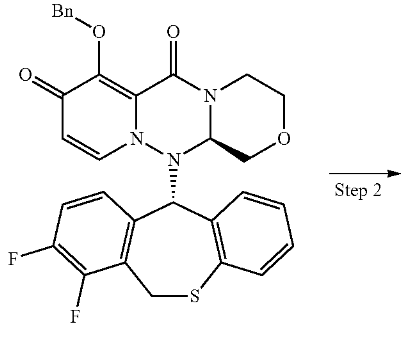

16

-continued

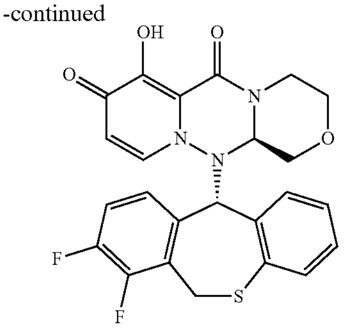

(VIIIa)

Step 1

Compound 15 (1100 g, 3360 mmol) and 7,8-difluoro-6,11-dihydrodibenzothiepine-11-ol (977 g, 3697 mmol) were suspended in 50 wt % T3P in ethyl acetate (3208 g, 5041 mmol) and ethyl acetate (1.1 L). To the mixture was added methanesulfonic acid (436 mL, 6721 mmol) at room temperature and the mixture was stirred at 70° C. for 5.5 hours. To the mixture was added water with ice cooling, and the mixture was stirred at room temperature for 1 hour. THF was added, and the mixture was extracted with ethyl acetate. The organic layer was washed with water and 8% aqueous sodium bicarbonate, dried over anhydrous sodium sulfate, and the solvent was removed under reduced pressure. The obtained residue was dissolved in THF (5.5 L), and potassium carbonate (790 g, 5713 mmol) was added. The mixture was warmed up to 50° C., and benzyl bromide (240 mL, 2016 mmol) was added dropwise, and the mixture was stirred at 60° C. for 8.5 hours. To the mixture was added dropwise 2 mol/L aqueous hydrochloric acid with ice cooling, and the mixture was stirred at room temperature for 10 minutes and extracted with ethyl acetate. The organic layer was washed with water and 8% aqueous sodium bicarbonate and dried over anhydrous magnesium sulfate. An activated carbon (Norit SX-2, 240 g) was added, and the mixture was filtered through Celite, and the filtrate was concentrated under reduced pressure. To the obtained residue was added ethyl acetate and hexane, and the presipitated solid was filtered to obtain Compound 16 (1019 g, 1776 mmol, 53%).

$^1$H-NMR ($CDCl_3$) δ: 2.88 (1H, t, J=11.2 Hz), 3.28-3.39 (2H, m), 3.72 (1H, d, J=12.6 Hz), 3.86 (1H, d, J=9.6 Hz), 4.03 (1H, d, J=13.9 Hz), 4.45 (1H, d, J=8.6 Hz), 4.67 (1H, d, J=13.1 Hz), 5.19-5.26 (2H, m), 5.45 (1H, d, J=10.9 Hz), 5.63 (1H, d, J=10.9 Hz), 5.77 (1H, d, J=7.6 Hz), 6.40 (1H, d, J=7.8 Hz), 6.68 (1H, t, J=6.9 Hz), 6.94-7.01 (2H, m), 7.03-7.12 (3H, m), 7.29-7.38 (3H, m), 7.61 (2H, d, J=7.1 Hz).

Step 2

To a solution of Compound 16 (1200 g, 2092 mmol) in DMA (3.6 L) was added lithium chloride (443 g, 10.5 mol) at room temperature, and the mixture was stirred at 80° C. for 3 hours. To the mixture were added acetone (1.2 L), 0.5 mol/L aqueous hydrochloric acid (6.0 L) and water (2.4 L) with ice cooling, and the mixture was stirred for 1 hour. The presipitated solid was filtered. The obtained solid was dissolved in chloroform, and isopropyl ether was added to precipitate solid, which was filtered to obtain Compound (VIIIa) (950 g, 1965 mmol, 94%).

$^1$H-NMR ($CDCl_3$) δ: 2.99 (1H, dt, J=17.5, 6.8 Hz), 3.47 (1H, td, J=11.9, 2.5 Hz), 3.60 (1H, t, J=10.6 Hz), 3.81 (1H, dd, J=11.9, 3.3 Hz), 3.96 (1H, dd, J=11.0, 2.9 Hz), 4.07 (1H, d, J=13.8 Hz), 4.58 (1H, dd, J=10.0, 2.9 Hz), 4.67 (1H, dd, J=13.5, 1.9 Hz), 5.26-5.30 (2H, m), 5.75 (1H, d, J=7.8 Hz), 6.69 (1H, d, J=7.7 Hz), 6.83-6.87 (1H, m), 6.99-7.04 (2H, m), 7.07-7.15 (3H, m).

Example 5

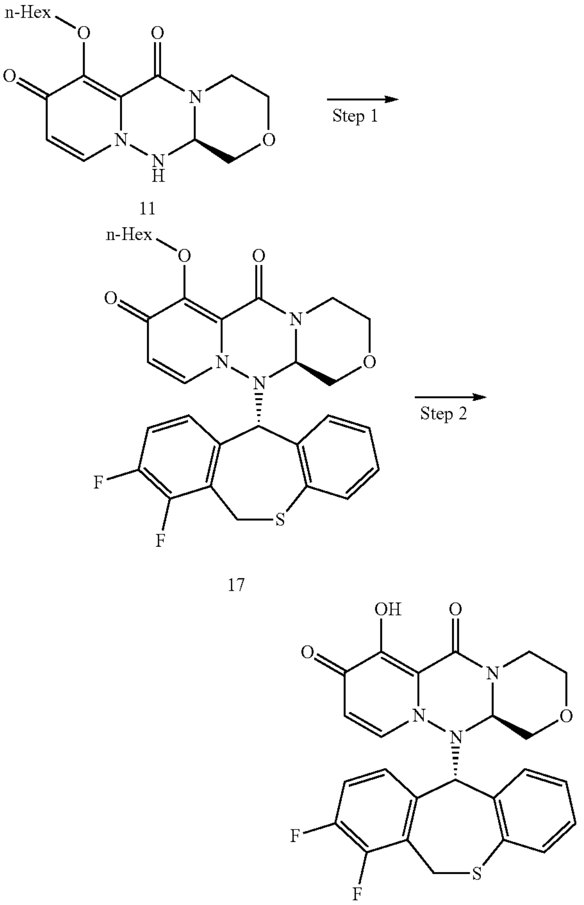

11

17

(VIIIa)

Step 1

To Compound 11 (12.0 g, 24.3 mmol) were added 7,8-difluoro-6,11-dihydrodibenzothiepin-11-ol (8.0 g, 30.3 mmol), ethyl acetate (48.7 g) and cyclohexane (14.1 g), and the mixture was stirred at 25° C. 50 (w/w) % T3P in ethyl acetate (20.91 g, 32.9 mmol) was added, followed by addition of methanesulfonic acid (3.5 g, 36.4 mmol). The mixture was heated to 60° C. and stirred for 24 hours. After cooling to 25° C., THF (32.0 g) and water (24.0 g) were added, and then 24% aqueous sodium hydroxide (30.8 g) was slowly added. The mixture was allowed to stand, and the organic layer and the aqueous layer were separated. The organic layer was washed twice with 7% aqueous sodium chloride (60.0 g). To the obtained solution were added a mixture of cyclohexane (9.3 g), ethyl acetate (32.1 g) and methanesulfonic acid (2.80 g, 29.1 mmol). The mixture was stirred at 25° C. for 2 hours, and the resulting white precipitate was filtered. The obtained solid was washed with ethyl acetate (43.3 g) and dried to obtain mesylate of compound 17 (13.65 g, 84.6%).

$^1$H-NMR (DMSO-$d_6$) δ: 0.90 (3H, t, J=6.0 Hz), 1.29-1.36 (4H, m), 1.39-1.49 (2H, m), 1.67-1.79 (2H, m), 2.38 (3H, s), 2.94 (1H, br s), 3.30 (1H, td, J=11.6, 2.4 Hz), 3.51 (1H, t, J=10.4 Hz), 3.66 (1H, dd, J=11.2, 2.8 Hz), 3.92-4.01 (2H, m), 4.07 (1H, d, J=14.3 Hz), 4.20 (1H, s), 4.42-4.52 (1H, m), 5.43 (1H, dd, J=14.4, 2.1 Hz), 5.79-5.83 (2H, m), 6.81 (1H, td, J=7.6, 1.2 Hz), 6.96 (1H, dd, J=7.8, 1.0 Hz), 7.09 (1H, J=8.0, 1.6 Hz), 7.12-7.18 (1H, m), 7.32 (1H, d, J=7.7 Hz), 7.37-7.49 (2H, m)

Step 2

To Compound 17 (15.0 g, 22.6 mmol) were added N-methylpyrrolidone (52.4 g), and the mixture was stirred. Lithium chloride (8.6 g, 203.3 mmol) was added, and the mixture was heated to 75° C. The mixture was stirred at 75° C. for 20 hours and then cooled to 40° C. Acetonitrile (20.0 g) was added, followed by addition of water (11.6 g). After cooling the mixture to 30° C. and stirring for 30 minutes, water (142.5 g) was slowly added. After stirring at 30° C. for 1.5 hours, the resulting white precipitate was filtered. The obtained solid was washed with 2-propanol (60.1 g) and dried to obtain Compound (VIIIa) (9.91 g, 90.7%).

Example 6

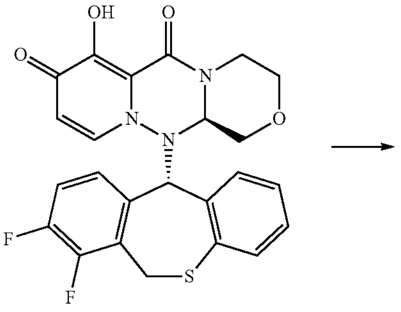

(VIIIa)

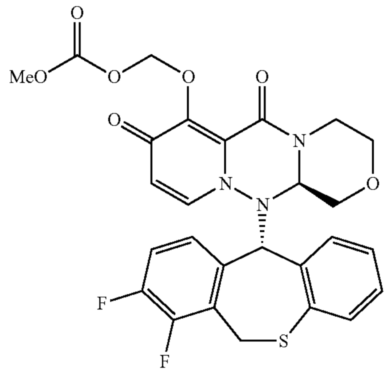

(IXa)

To a suspension of Compound (VIIIa) (1.00 g, 2.07 mmol) in DMA (5 mL) were added chloromethyl methyl carbonate (0.483 g, 3.10 mmol), potassium carbonate (0.572 g, 4.14 mmol) and potassium iodide (0.343 g, 2.07 mmol), and the mixture was stirred at 50° C. for 6 hours. To the mixture was added DMA (1 mL), and the mixture was stirred for 6 hours. The mixture was cooled to room temperature, DMA (6 mL) was added, and the mixture was stirred at 50° C. for 5 minutes. The mixture was filtered. To the obtained filtrate were added dropwise 1 mol/L aqueous hydrochloric acid (10 mL) and water (4 mL) with ice cooling, and the mixture was stirred for 1 hour. The pre-sipitated solid was filtered and dried under reduced pressure at 60° C. for 3 hours to obtain Compound (IXa) (1.10 g, 1.93 mmol, 93%).

1H-NMR (DMSO-$D_6$) δ: 2.91-2.98 (1H, m), 3.24-3.31 (1H, m), 3.44 (1H, t, J=10.4 Hz), 3.69 (1H, dd, J=11.5, 2.8 Hz), 3.73 (3H, s), 4.00 (1H, dd, J=10.8, 2.9 Hz), 4.06 (1H, d, J=14.3 Hz), 4.40 (1H, d, J=11.8 Hz), 4.45 (1H, dd, J=9.9, 2.9 Hz), 5.42 (1H, dd, J=14.4, 1.8 Hz), 5.67 (1H, d, J=6.5 Hz), 5.72-5.75 (3H, m), 6.83-6.87 (1H, m), 7.01 (1H, d, J=6.9 Hz), 7.09 (1H, dd, J=8.0, 1.1 Hz), 7.14-7.18 (1H, m), 7.23 (1H, d, J=7.8 Hz), 7.37-7.44 (2H, m).

Example 7

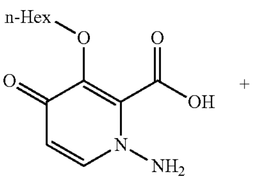

18

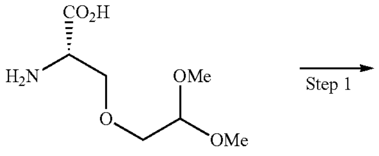

19

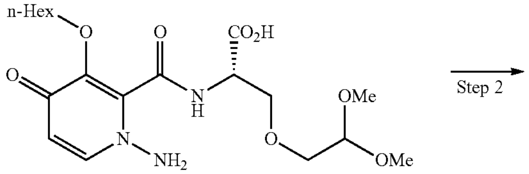

20

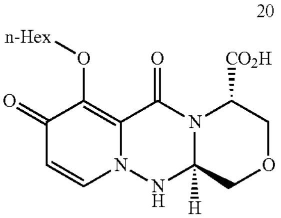

10

Step 1 tert-Amyl alcohol (1195 μL, 10.99 mmol) was added to Compound 18 (99.6 mg, 0.392 mmol), N-hydroxysuccin-imide (54.3 mg, 0.472 mmol), 1-hydroxybenzotriazole monohydrate (6.3 mg, 0.041 mmol) and 1-ethyl-3-(3-dim-ethylaminopropyl) carbodiimide hydrochloride (99.8 mg, 0.521 mmol), and the mixture was stirred at 35° C. The reaction mixture was cooled to room temperature, and acetic acid (7.1 mg, 0.12 mmol), compound 19 (99.2 mg, 0.513 mmol) and diazabicycloundecene (155.9 mg, 1.024 mmol) were added. The mixture was stirred at room temperature for 3 hours 40 minutes. Water (1100 μL) and toluene (500 μL) were added to isolate the aqueous layer. Water (200 μL) and 25% aqueous sodium hydroxide solution (20 μL) were added to the organic layer. The layers were separated, and the aqueous layer was isolated. The obtained aqueous layers were combined, and toluene (500 μL) was added. The aqueous layer was isolated and concentrated under reduced pressure to obtain an aqueous solution of compound 20.

Step 2

To the aqueous solution of compound 20 were added acetonitrile (1000 μL) and concentrated hydrochloric acid (200 μL), and the mixture was stirred at 45° C. and then allowed to stand overnight at room temperature. The mixture was concentrated under reduced pressure, and water (500 μL), formic acid (10 μL), 25% aqueous sodium hydroxide solution (180 μL), acetonitrile (300 μL) and methanol (3000 μL) were added. The mixture was concentrated to about half volume under reduced pressure. Seed crystals were added to precipitate, and the mixture was further concentrated under reduced pressure and allowed to stand overnight at room temperature. The obtained solid was collected by filtration and washed with water to obtain Compound 10 (23.0 mg, 16.1%).

The diastereomer ratio of a:b=20:1 was obtained in the intramolecular cyclization reaction of the step for preparing Compound 9 in Example 1. The diastereomer ratio of a:b=67:3 was obtained in the intramolecular cyclization reaction of the step for preparing Compound 10 in Example 7.

Thus, the intramolecular cyclization reaction as described herein proceeds with high diastereoselectivity, so that an optically active compound of the formula (VII) can be synthesized efficiently.

Example 8

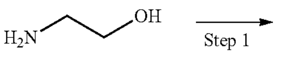

21

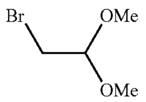

23

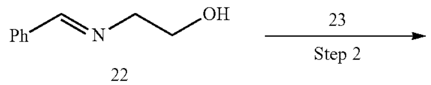

22

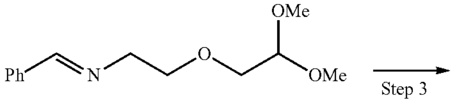

24

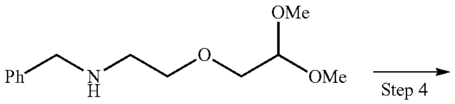

25

-continued

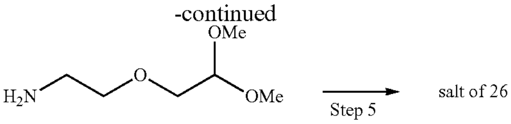

26

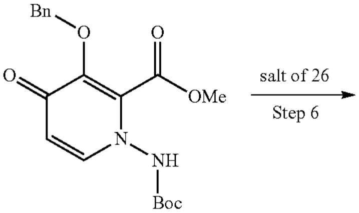

27

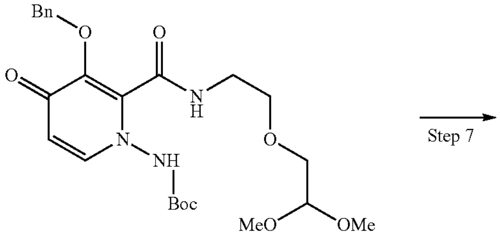

28

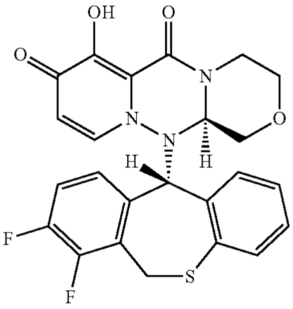

or (VIIIa)

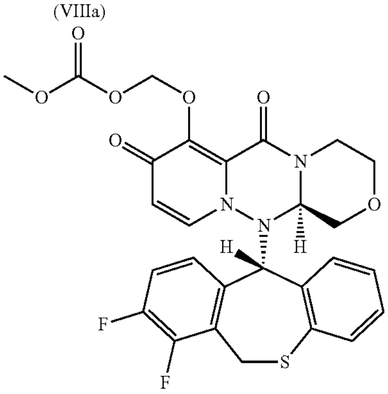

(IXa)

Step 1 to Step 3

Benzaldehyde (4.16 g, 38.43 mmol) was dissolved in 1,2-dimethoxyethane (10 mL), and Compound 21 (2.35 g, 38.42 mmol) was added dropwise over about 30 minutes with stirring at about 25° C. The reaction mixture was stirred for 20 minutes.

The resulting reaction mixture was ice-cooled, and sodium tert-pentoxide (8.46 g, 76.82 mmol) and 1,2-dimethoxyethane (10 mL) were added to the reaction mixture.

Compound 23 (8.45 g, 49.94 mmol) was then added, and the mixture was stirred at 50° C. for 13 hours.

To the resulting reaction mixture was added sodium borohydride (2.91 gm, 76.92 mmol) and further methanol (19.69 g, 614.45 mmol) dropwise. The mixture was stirred at the same temperature for 30 minutes. To the mixture was added slowly deionized water (20 mL), and then 20% aqueous hydrochloric acid was added until the pH became 2. Subsequently, isopropyl acetate (50 mL) was added, and the pH was adjusted to 10 with 20% aqueous sodium hydroxide and extracted with isopropyl acetate (50 mL). The obtained organic layer was washed with 20% aqueous sodium chloride, dried over anhydrous sodium sulfate, and concentrated. Toluene (50 mL) was added to the concentrated solution, and the mixture was concentrated again to obtain Compound 25 (4.07 g, 44%).

1H-NMR ($CDCl_3$) δ: 2.82 (2H, t, J=5.28 Hz), 3.38 (6H, s), 3.50 (2H, d, J=5.16 Hz), 3.63 (2H, t, J=5.28 Hz), 3.81 (2H, s), 4.50 (1H, t, J=5.24 Hz), 7.29-7.34 (5H, m)

Step 4

The mixture of 53.5% water-wet 5% Pd/C (3.01 g), Compound 25 (7.00 g, 29.25 mmol), THF (70 mL) and acetic acid (1.76 g, 29.25 mmol) was degassed under reduced pressure and then subjected to hydrogen replacement twice. The mixture was stirred at 45° C. for 4 hours under hydrogen pressure of 0.3 to 0.2 Mpa. The mixture was filtered, washed four times with THF (30 mL), and concentrated to obtain Compound 26.

Step 5

THF was added to the obtained Compound 26, and then, an acid was added dropwise at about 25° C. to evaluate whether the compound crystallized or not. The results of the evaluation for crystallization and the property of the obtained crystals are shown in Table 1 below.

TABLE 1

| Acid | Crystallization | |
|---|---|---|
| Phosphoric Acid | Yes | No deliquescence |
| MsOH | Yes | Deliquescent |
| 4•Cl•PhCOOH | Yes | Deliquescent |
| TsOH | No | |
| AcOH | No | |
| PhCOOH | No | |
| $PhSO_3H$ | No | |
| 4•MeOPhCOOH | No | |
| Hydrochloric Acid | No | Colored |
| Sulfuric Acid | No | Colored |

Crystallization of Phosphate Salt

To a solution of Compound 26 in THF (13.6 mL) was added slowly 85% phosphoric acid (3.37 g, 29.25 mmol) at about 25° C. to precipitate phosphate salt of Compound 26. The resulting suspension was cooled to about 5° C. and then filtered. The obtained solid was washed three times with THF (15 mL) and dried under reduced pressure at about 40° C. to obtain crystals of phosphate salt of Compound 26 (6.57 g, 91%).

1H-NMR (DMSO-$D_6$) δ: 2.86 (2H, t, J=5.62 Hz), 3.29 (6H, s), 3.43 (2H, d, J=5.14 Hz), 3.59 (2H, t, J=5.62 Hz), 4.48 (1H, t, J=5.14 Hz)

The results of X-ray powder diffraction are shown below in terms of the angle 2θ(°) of diffraction peaks.

TABLE 2

| 2θ | Relative Intensity |
|---|---|
| 5.10 | 100 |
| 10.16 | 1 |
| 15.32 | 9 |
| 20.46 | 28 |
| 21.82 | 1 |
| 25.66 | 11 |
| 30.92 | 5 |
| 36.26 | 1 |

As shown above, crystallization of Compound 26 was evaluated, and phosphate salt, methanesulfonate salt and p-chlorobenzoate salt thereof were crystallized. Especially, crystals of phosphate salt are excellent as they were not deliquescent. In addition, crystals of phosphate salt of Compound 26 enable to avoid extraction of the compound with dichloromethane, so that it makes easier to handle.

Step 6

A solution containing Compound 27 (50.00 g, 133.55 mmol) and 20% sodium hydroxide (80.13 g, 400.65 mmol) in THF (100 mL) was stirred at 55° C. for 5 hours. The reaction mixture was concentrated. Water (34.6 g) and THF (50 mL) were added to the obtained residue. The mixture was heated to 50° C., and the organic layer and aqueous layer were separated. The aqueous layer was concentrated (132.54 g). The resulting concentrate (79.52 g, 80.13 mmol) was further concentrated to 69.11 g.

The concentrate was added to a suspension of the phosphate salt of Compound 26 (23.77 g, 96.16 mmol) in acetonitrile (300 mL) at 0° C. Then, 1-hydroxybenzotriazole monohydrate (2.45 g, 16.00 mmol), WSCD HCl (18.43 g, 96.14 mmol) and acetonitrile (540 mL) were added, and the mixture was stirred at 50° C. for 8 hours. The reaction mixture was concentrated to 144.71 g, and isopropyl acetate (300 mL) and water (60 mL) were added, and the mixture was extracted. The organic layer was washed three times with 20% aqueous sodium chloride and concentrated. Insoluble matter was removed by filtration, and the obtained filtrate was concentrated to 60.46 g. Isopropyl acetate was added to the concentrate, and the mixture was stirred at 22° C. for 30 minutes to obtain a suspension of Compound 28. To the resulting suspension was added n-heptane (90 mL), followed by filtration, and the filtrate was washed three times with 30 mL of a mixed solution (heptane:isopropyl acetate=2:1 (v/v)). The obtained solid was dried to obtain Compound 28 (33.61 g, 85%).

Step 7

Compounds of the formula (VIIIa) and the formula (IXa) were obtained according to the methods as described in WO2012/039414 and WO2016/175224.

Example 9

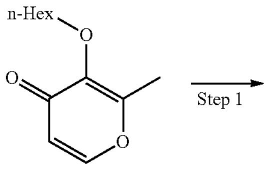

29

-continued

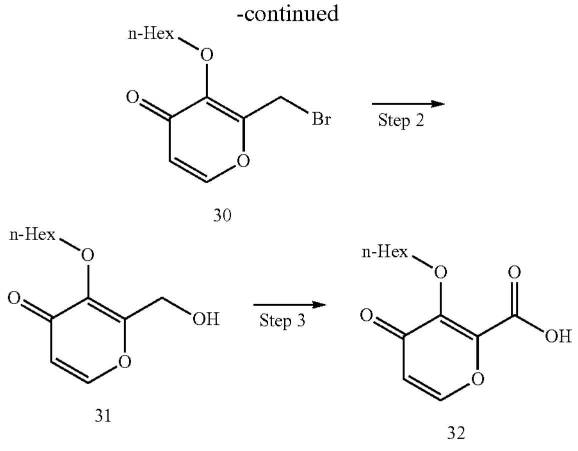

30

31

32

Step 1

Under a nitrogen atmosphere, Compound 29 (105 mg, 0.5 mmol) was dissolved in ethyl acetate (5 mL), and N-bromosuccinimide (196 mg, 1.1 mmol) and AIBN (33 mg, 0.2 mmol) were added. The mixture was heated to reflux for 7 hours with stirring. After cooling to room temperature, ethyl acetate (10 mL) and saturated aqueous sodium hydrogen carbonate (5 mL) were added. The organic layer was separated, washed with saturated brine (5 mL), and dried with anhydrous sodium sulfate. The solvent was removed under reduced pressure, and the residue was purified by silica gel column chromatography (hexane/ethyl acetate=75:25 to 70:30) to obtain Compound 30 (126 mg, 87%).

1H-NMR ($CDCl_3$) δ: 0.90 (t, J=7.0 Hz, 3H), 1.25-1.51 (m, 6H), 1.71-1.79 (m, 2H), 4.21 (t, J=6.8 Hz, 2H), 4.41 (s, 2H), 6.38 (d, J=5.8 Hz, 1H), 7.68 (d, J=5.6 Hz, 1H).

Step 2

Compound 30 (58 mg, 0.2 mmol) was dissolved in a mixed solution of acetonitrile (1.2 mL) and water (1.2 mL) under nitrogen atmosphere, and then, calcium carbonate (40 mg, 0.4 mmol) was added. The mixture was stirred at 85° C. for 24 hours. After cooling the mixture to room temperature, water (5 mL) and ethyl acetate (10 mL) were added. The organic layer was separated and washed with saturated brine (5 mL), dried over anhydrous sodium sulfate and evaporated under reduced pressure. The residue was purified by silica gel column chromatography (hexane/ethyl acetate=50:50) to obtain Compound 31 (37 mg, 83%).

1H-NMR ($CDCl_3$) δ: 0.79-0.86 (m, 3H), 1.19-1.34 (m, 6H), 1.61-1.68 (m, 2H), 4.04 (t, J=6.8 Hz, 2H), 4.56 (d, J=6.1 Hz, 2H), 6.31 (d, J=5.6 Hz, 1H), 7.66 (d, J=5.6 Hz, 1H).

Step 3

Under a nitrogen atmosphere, Compound 31 (45 mg, 0.2 mmol) was dissolved in a mixed solution of acetonitrile (0.9 mL) and water (0.45 mL), and then, TEMPO (1.6 mg, 0.01 mmol), sodium hydrogen carbonate (17 mg, 0.2 mmol), KBr (24 mg, 0.2 mmol) and $NaClO·5H_2O$ (72 mg, 0.44 mmol) were added. After stirring for 2 hours at room temperature, 15% aqueous $Na_2S_2O_3$ solution (2 mL) and ethyl acetate (10 mL) were added. The organic layer was separated, washed with water (5 mL) and saturated brine (5 mL), dried over anhydrous sodium sulfate, and evaporated under reduced pressure. The residue was purified by silica gel column chromatography (chloroform/methanol=100:0 to 80:20) to give Compound 32 (48 mg, 99%).

1H-NMR ($CDCl_3$) δ: 0.90 (t, J=7.1 Hz, 3H), 1.26-1.42 (m, 6H), 1.78-1.85 (m, 2H), 4.59 (t, J=7.0 Hz, 2H), 6.51 (d, J=5.6 Hz, 1H), 7.84 (d, J=5.8 Hz, 1H)

Example 10

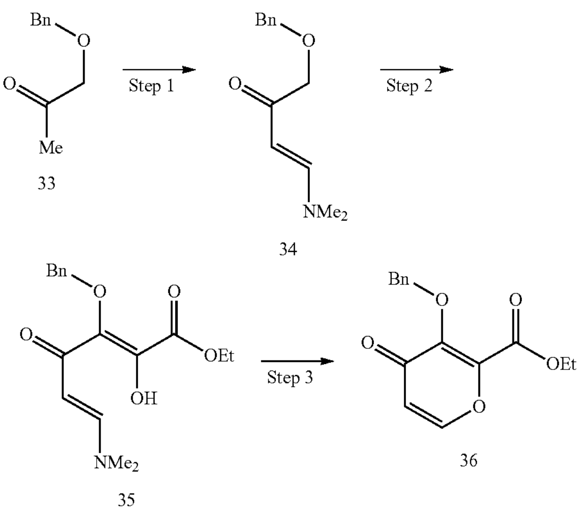

33

34

35

36

Step 1

To a solution of Compound 33 (91 mg, 0.5 mmol) in DMSO (0.5 mL) were added dimethylformamide dimethylacetal (0.133 mL, 1.0 mmol) and acetic acid (9 mg, 0.15 mmol) under a nitrogen atmosphere. The mixture was stirred at 85° C. for 24 hours. After cooling the mixture to room temperature, ethyl acetate (10 mL) and water (5 mL) were added. The organic layer was separated and washed with saturated brine (5 mL), dried over anhydrous sodium sulfate, and evaporated under reduced pressure. The residue was purified by silica gel column chromatography (hexane/ethyl acetate=70:30 to 10:90) to obtain Compound 34 (79 mg, 72%).

1H-NMR ($CDCl_3$) δ: 2.84 (s, 3H), 3.10 (s, 3H), 4.04 (s, 2H), 4.60 (s, 2H), 5.40 (d, J=12.7 Hz, 1H), 7.26-7.39 (m, 5H), 7.71 (d, J=12.7 Hz, 1H).

Step 2

To a solution of Compound 34 (110 mg, 0.5 mmol) in toluene (2.2 mL) were added diethyl oxalate (219 mg, 1.5 mmol) and 20 wt % sodium ethoxide in ethanol (0.29 mL, 0.75 mmol). The mixture was stirred at room temperature for 1 hour. To the mixture were added 10% aqueous ammonium chloride (5 mL) and ethyl acetate (10 mL). The organic layer was separated, washed with saturated brine (5 mL), dried over anhydrous sodium sulfate, and evaporated under reduced pressure. The residue was purified by silica gel column chromatography (hexane/ethyl acetate=70:30 to 50:50) to obtain Compound 35 (154 mg, 96%).

1H-NMR ($CDCl_3$) δ: 1.34 (t, J=7.2 Hz, 3H), 2.81 (s, 3H), 3.17 (s, 3H), 4.33 (q, J=7.2 Hz, 2H), 4.83 (s, 2H), 5.43 (d, J=12.4 Hz, 1H), 7.32-7.39 (m, 3H), 7.45 (d, J=7.0 Hz, 2H), 7.78 (d, J=12.4 Hz, 1H).

Step 3

To a solution of Compound 35 (32 mg, 0.1 mmol) in N,N-dimethylacetamide (1 mL) was added pyridinium p-toluenesulfonate (75 mg, 0.3 mmol) under nitrogen atmosphere. The mixture was stirred at 60° C. for 1 hour. Water (5 mL) and ethyl acetate (10 mL) were added to the reaction mixture. The organic layer was separated and washed with water (5 mL) and saturated brine (5 mL), dried over anhydrous sodium sulfate and evaporated under reduced pressure. The residue was purified by silica gel column chromatography (hexane/ethyl acetate=80:20 to 70:30) to obtain Compound 36 (26 mg, 97%).

Example 11

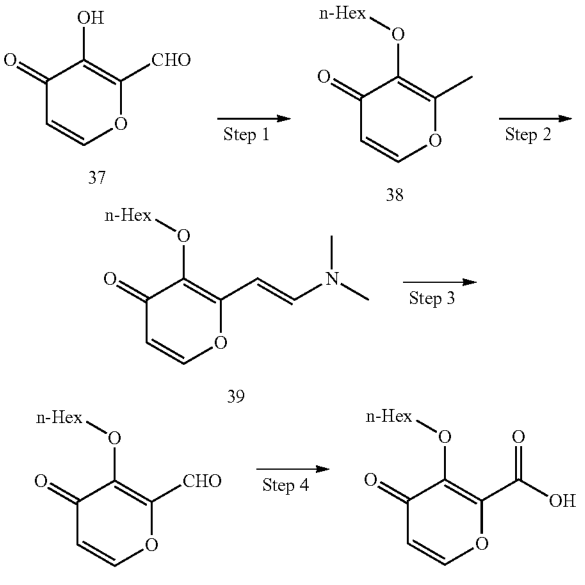

37 38 39 40 32

Step 1

Under a nitrogen atmosphere, a suspension of potassium carbonate (8.22 g, 59.5 mmol) in DMA (25 mL) was heated at 78° C. with stirring. To the suspension was added dropwise a solution of maltol (5.00 g, 39.6 mmol) and 1-bromohexane (6.68 mL, 47.6 mmol) in DMA (50 mL) over 1 hour. The mixture was heated at 78° C. for 3 hours with stirring. After cooling the mixture to 40° C., 1-ethylpiperazine (1.52 mL, 11.9 mmol) was added. The reaction mixture was heated to 70° C. and stirred with heating for 1 hour, and then cooled to 40° C. Ethyl acetate (50 mL) and water (100 mL) were added to the reaction mixture, and the mixture was extracted with ethyl acetate (20 mL). The organic layer was separated, washed twice with 0.4 mol/L hydrochloric acid (20 mL) and once with 5% aqueous sodium hydrogen carbonate (20 mL), dried over anhydrous sodium sulfate, and evaporated under reduced pressure to give Compound 38 (8.15 g, 98%).

1H-NMR ($CDCl_3$) δ: 0.84-0.93 (m, 3H), 1.29-1.45 (m, 6H), 1.67-1.74 (m, 2H), 2.32 (s, 3H), 4.04 (t, J=6.8 Hz, 2H), 6.34 (d, J=5.6 Hz, 1H), 7.60 (d, J=5.6 Hz, 1H).

Step 2

Under a nitrogen atmosphere, to a solution of the crude product of Compound 38 (1.00 g, 4.76 mmol) in DMSO (5.00 mL) were added dimethylformamide dimethylacetal (3.41 mL, 25.5 mmol), propionic acid (0.076 mL, 1.02 mmol) and triethylamine (0.424 mL, 3.06 mmol), and the mixture was heated at 100° C. for 19 hours with stirring. After cooling the reaction mixture to room temperature, toluene (10 mL) and 10% aqueous NaCl solution (20 mL) were added, and the mixture was extracted with toluene (10 mL). The organic layer was washed twice with water (10 mL), and anhydrous sodium sulfate (1.00 g) and activated carbon (200 mg) were added. The mixture was stirred at room temperature for 1 hour, filtered through KC-flock and washed with toluene (30 mL). The filtrate was concentrated under reduced pressure to give Compound 39 (1.30 g, 100%).

1H-NMR ($CDCl_3$) δ: 0.89 (t, J=7.2 Hz, 3H), 1.29-1.35 (m, 4H), 1.41-1.48 (m, 2H), 1.68-1.76 (m, 2H), 2.94 (s, 6H), 4.03 (t, J=6.8 Hz, 2H), 5.22 (d, J=13.3 Hz, 1H), 6.19 (d, J=5.6 Hz, 1H), 7.12 (d, J=13.3 Hz, 1H), 7.42 (d, J=5.6 Hz, 1H).

Step 3

Under a nitrogen atmosphere, sodium periodate (32.8 g, 154 mmol) was dissolved in water (122 mL) and acetonitrile (82 mL), and the mixture was heated at 45° C. with stirring. To the reaction mixture was added the crude product of Compound 39 (8.15 g, 30.7 mmol) in acetonitrile (82 mL) dropwise over 2 hours and 40 minutes. The mixture was heated at 45° C. for 1 hour with stirring, filtered through KC-flock, and washed with ethyl acetate (200 mL). The filtrate was washed with 7.7% aqueous sodium chloride (106 mL), 10% aqueous sodium thiosulfate (250 mL) and 5% aqueous sodium hydrogen carbonate (82 mL). Each aqueous layer was extracted with ethyl acetate (82 mL). The organic layer was dried over anhydrous sodium sulfate and concentrated under reduced pressure to obtain Compound 40 (6.26 g, 91%).

1H-NMR ($CDCl_3$) δ: 0.90 (t, J=7.0 Hz, 3H), 1.28-1.44 (m, 6H), 1.72-1.80 (m, 2H), 4.46 (t, J=6.7 Hz, 2H), 6.47 (d, J=5.8 Hz, 1H), 7.76 (d, J=5.8 Hz, 1H), 10.19 (s, 1H).

Step 4

To a solution of the crude product of Compound 40 (6.88 g, 30.7 mmol) in acetonitrile (73 mL) were added acetic acid (2.63 mL, 46.1 mmol) and 30% aqueous hydrogen peroxide (7.84 mL, 76.8 mmol) with ice-cooling under nitrogen atmosphere. An aqueous solution (73 mL) containing 80% sodium chlorite (7.64 g, 67.5 mmol) was added dropwise over 23 minutes, and the mixture was stirred at room temperature for 2 hours. Diisopropyl ether (73 mL) and 5% aqueous sodium hydrogen carbonate (73 mL) were added to the reaction solution, and the mixture was extracted with 5% aqueous sodium hydrogen carbonate (73 mL). To the aqueous layer were added 5% aqueous sodium bisulfite (73 mL) and diisopropyl ether (73 mL), and the mixture was extracted with 5% aqueous sodium hydrogen carbonate solution (73 mL). Ethyl acetate (73 mL) and 2 mol/L hydrochloric acid (146 mL) were added to the obtained aqueous layer, and the mixture was extracted with ethyl acetate (73 mL). The organic layer was dried over anhydrous sodium sulfate and concentrated under reduced pressure. Diisopropyl ether (37 mL) was added, and the mixture was stirred at room temperature for 1 hour. The precipitated solid was filtered and washed with diisopropyl ether (36 mL) to obtain Compound 32 (4.45 g, 60%).

1H-NMR ($CDCl_3$) δ: 0.89 (t, J=6.9 Hz, 3H), 1.31-1.41 (m, 7H), 1.78-1.85 (m, 2H), 4.58 (t, J=6.9 Hz, 2H), 6.51 (d, J=5.6 Hz, 1H), 7.84 (d, J=5.6 Hz, 1H).

Example 12

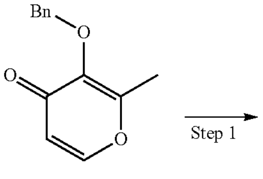

41

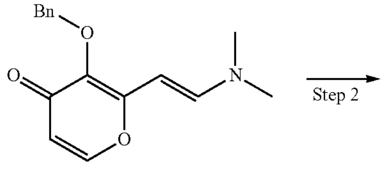

42

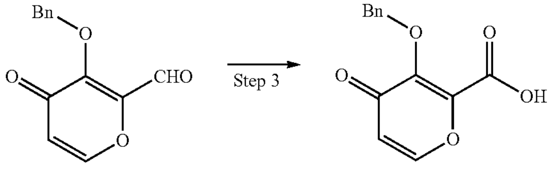

43 44

Step 1

To a solution of Compound 41 (1.00 g, 4.62 mmol) in DMSO (5 mL) were added dimethylformamide dimethylacetal (3.10 mL, 23.1 mmol) and N,N,N-trimethylglycine (108 mg, 0.925 mmol) under nitrogen atmosphere. The mixture was heated at 100° C. for 8 hours with stirring. After cooling the reaction mixture to room temperature, toluene (10 mL) and 10% aqueous NaCl solution (20 mL) were added. The mixture was extracted with toluene (10 mL). The organic layer was washed twice with water (10 mL) and concentrated under reduced pressure to 1.53 g. Toluene (1.5 mL) was added to the residue, and the mixture was stirred at 0° C. for 15 minutes. To the solution was added diisopropyl ether (30 mL), and the mixture was stirred at 0° C. for 30 minutes. The precipitated solid was filtered and washed with a mixed solvent (21 mL) of toluene/diisopropyl ether (1:20) to obtain Compound 42 (987 mg, 79%).

1H-NMR ($CDCl_3$) δ: 2.83 (s, 6H), 5.01 (d, J=13.4 Hz, 1H), 5.11 (s, 2H), 6.22 (d, J=5.8 Hz, 1H), 7.03 (d, J=13.4 Hz, 1H), 7.29-7.35 (m, 3H), 7.42 (d, J=5.8 Hz, 1H), 7.44-7.47 (m, 2H).

Step 2

To a solution of Compound 42 (2.00 g, 7.37 mmol) in acetonitrile (30 mL) was added dropwise an aqueous solution (30 mL) of sodium periodate (3.47 g, 16.2 mmol) over 16 minutes with ice-cooling under nitrogen atmosphere. The reaction mixture was stirred at room temperature for 5 hours, filtered through KC-flock and washed with ethyl acetate (40 mL). Water (20 mL) was added to the filtrate. The organic layer was separated and washed with 10% aqueous sodium thiosulfate (20 mL) and 5% aqueous sodium hydrogen carbonate (20 mL). Each aqueous layer was extracted with ethyl acetate (20 mL). The organic layer was dried over anhydrous sodium sulfate and concentrated under reduced pressure. The residue was purified by silica gel column chromatography (hexane/ethyl acetate=80:20 to 50:50) to obtain Compound 43 (1.62 g, 95%).

1H-NMR ($CDCl_3$) δ: 5.52 (s, 2H), 6.50 (d, J=5.8 Hz, 1H), 7.33-7.40 (m, 5H), 7.75 (d, J=5.8 Hz, 1H), 9.88 (s, 1H).

Step 3

To a solution of Compound 43 (1.78 g, 7.74 mmol) in acetonitrile (18 mL) were added TEMPO (121 mg, 0.774 mmol) and 5% aqueous sodium hydrogen carbonate (10.7 mL) under nitrogen atmosphere. The reaction mixture was ice-cooled, and 5% aqueous sodium hypochlorite (12.4 mL) was added dropwise over 8 minutes. The mixture was stirred at room temperature for 2.5 hours. To the reaction mixture were added diisopropyl ether (36 mL) and 5% aqueous sodium bicarbonate (18 mL), and the mixture was extracted with 5% aqueous sodium hydrogen carbonate (18 mL). To the aqueous layer were added 5% aqueous sodium bisulfite (18 mL) and diisopropyl ether (36 mL), and the mixture was extracted with 5% aqueous sodium hydrogen carbonate (18 mL). To the aqueous layer was added 2 mol/L hydrochloric acid (36 mL), and the mixture was stirred for 30 minutes under ice cooling. The precipitated solid was filtered and washed with water (72 mL) to obtain Compound 44 (1.08 g, 57%).

1H-NMR ($CDCl_3$) δ: 5.65 (s, 2H), 6.53 (d, J=5.8 Hz, 1H), 7.39-7.41 (m, 5H), 7.82 (d, J=5.8 Hz, 1H).

Thus, the process for preparing a pyrone derivative according to the present invention can produce the pyrone derivative in more industrially suitable and efficient manner with avoiding use of a toxic reagent or a cryogenic reaction, and therefore it enables to produce a compound having a common skeleton in more industrially suitable and efficient manner.

Example 13

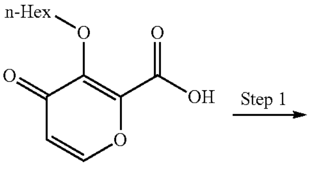

45

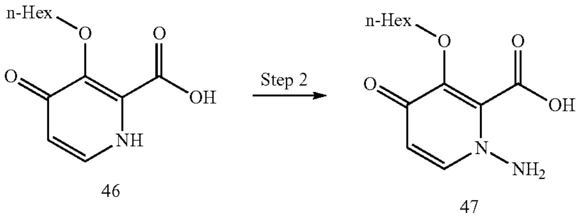

46 47

Step 1

Water (2644 mg) was added to compound 45 (660.8 mg, 2.75 mmol) and ammonium acetate (2120 mg, 27.5 mmol), and the mixture was stirred at 85° C. for 7.5 hours. After standing at room temperature overnight, the mixture was further stirred at 85° C. for 7.5 hours and allowed to stand at room temperature overnight. The reaction solution was heated to 60° C., and insoluble material formed during the reaction was separated by decantation. The insoluble material was washed with water (2000 μL), and the washing solution was combined with the reaction solution. Acetonitrile (700 μL) was added to the obtained solution, and the pH was adjusted to 2 by adding conc. hydrochloric acid. The precipitated solid was separated by filtration, washed with water, and dried under reduced pressure to obtain Compound 46 (649.3 mg, 99%).

$^1$H-NMR (DMSO-$d_6$) δ: 0.87 (t, J=7.0 Hz, 3H), 1.25-1.31 (m, 4H), 1.31-1.40 (m, 2H), 1.58-1.66 (m, 2H), 4.00 (t, J=6.6 Hz, 2H), 6.51 (br, 1H), 7.70 (br, 1H), 12.21 (br, 1H).

Step 2

Compound 46 (110 mg, 0.460 mmol) and potassium hydroxide (135 mg, 2.41 mmol) were dissolved in a mixture of water (1480 μL) and tert-amyl alcohol (110 μL). To the mixture was added hydroxylamine-O-sulfonic acid (101 mg, 0.894 mmol) at room temperature over 2 hours and 20 minutes. The mixture was stirred for 1 hour and 30 minutes and allowed to stand at room temperature overnight. The reaction mixture was stirred at room temperature, and potassium hydroxide (20.3 mg, 0.362 mmol), water (129 μL) and hydroxylamine-O-sulfonic acid (10.3 mg, 0.0911 mmol) were added, and the mixture was stirred for 2 hours. Thereafter, hydroxylamine-O-sulfonic acid (5.1 mg, 0.045 mmol) was added, and the mixture was stirred for 2.5 hours. Water (330 μL) was added to the reaction mixture, and the pH was adjusted to 1 by adding 10% hydrochloric acid. The obtained solid was separated by filtration, washed with water, and dried under reduced pressure to obtain compound 47 (98.9 mg, 85%).

$^1$H-NMR (DMSO-$d_6$) δ: 0.86 (t, J=7.0 Hz, 3H), 1.21-1.36 (m, 6H), 1.51-1.58 (m, 2H), 3.99 (t, J=6.6 Hz, 2H), 6.18 (d, J=7.2 Hz, 1H), 7.54 (d, J=7.2 Hz, 1H).

As described above, the disclosed process for the production of an aminopyridone derivative can efficiently produce the aminopyridone derivative, and thus, efficiently produce a compound having a common partial skeleton in more industrially suitable manner.

INDUSTRIAL APPLICABILITY

The present invention is useful as a process for preparing substituted polycyclic pyridone derivatives having a cap-dependent endonuclease inhibitory activity and its intermediates.

The invention claimed is:

1. A process for preparing a compound of the formula (III), or a salt thereof:

(III)

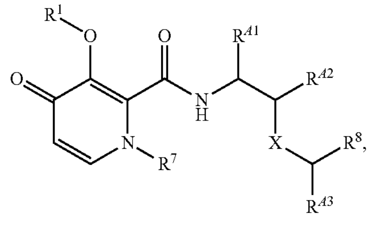

wherein $R^1$, $R^7$, $R^8$, $R^{A1}$, $R^{A2}$, $R^{A3}$ and X are each as defined below;

the process comprising reacting a compound of the formula (Ia):

(Ia)

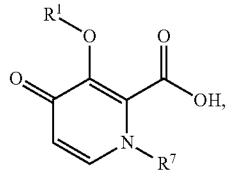

wherein $R^1$ is hydrogen or a protecting group for hydroxyl group; $R^7$ is $NH_2$ or $NHR_2$; $R^2$ is a protecting group for amino group;

with a compound of the formula (II):

(II)

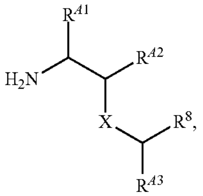

wherein $R^{A1}$ is hydrogen or RA; $R^{A2}$ is hydrogen or RA; $R^{A3}$ is hydrogen or RA; X is O, $CH_2$ or CHRA; RA is an optionally protected carboxy group; provided that one of $R^{A1}$, $R^{A2}$ and $R^{A3}$ is RA, the other two are hydrogen, and X is O or $CH_2$, or $R^{A1}$, $R^{A2}$ and $R^{A3}$ are hydrogen and X is CHRA; $R^8$ is —CHO or —CH($OR^4$)($OR^4$); $R^4$ is each independently hydrogen or a protecting group deprotectable by an acid, or two $R^4$ may be taken together to form a ring.

2. A compound of the formula (III) or a salt thereof:

(III)

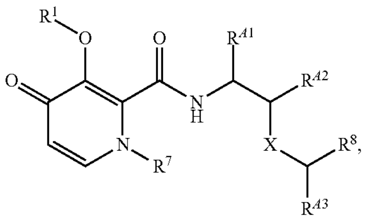

wherein:

$R^1$ is hydrogen or a protecting group for hydroxyl group;

$R^7$ is $NH_2$ or $NHR^2$;

$R^2$ is a protecting group for amino group;

$R^{A1}$ is hydrogen or RA;

$R^{A2}$ is hydrogen or RA;

$R^{A3}$ is hydrogen or RA;

X is O, $CH_2$ or CHRA;

RA is an optionally protected carboxy;

provided that one of $R^{A1}$, $R^{A2}$ and $R^{A3}$ is RA, the other two are hydrogen, and X is O or $CH_2$, or $R^{A1}$, $R^{A2}$ and $R^{A3}$ are hydrogen and X is CHRA;

$R^8$ is —CHO or —CH($OR^4$)($OR^4$); and $R^4$ is each independently hydrogen or a protecting group deprotectable by an acid, or two $R^4$ may be taken together to form a ring.

* * * * *